US010435363B2

(12) United States Patent
Dwivedi et al.

(10) Patent No.: US 10,435,363 B2
(45) Date of Patent: *Oct. 8, 2019

(54) PROCESS FOR PREPARATION OF PYRROLES HAVING HYPOLIPIDEMIC HYPOCHOLESTEREMIC ACTIVITIES

(71) Applicant: Cadila Healthcare Limited, Ahmedabad, Gujarat (IN)

(72) Inventors: Shriprakash Dhar Dwivedi, Gujarat (IN); Ramesh Chandra Singh, Gujarat (IN); Rajendra Gokalbhai Chavda, Gujarat (IN); Jagdish Maganlal Patel, Gujarat (IN); Daya Ram Pal, Gujarat (IN); Pranav Jitendra Gangwar, Gujarat (IN); Vikas Patel, Gujarat (IN); Vishwadeepak Rama Pati Tripathi, Gujarat (IN)

(73) Assignee: Cadila Healthcare Limited, Ahmedabad, Gujarat (IN)

( * ) Notice: Subject to any disclaimer, the term of this patent is extended or adjusted under 35 U.S.C. 154(b) by 0 days.

This patent is subject to a terminal disclaimer.

(21) Appl. No.: 15/366,229

(22) Filed: Dec. 1, 2016

(65) Prior Publication Data

US 2017/0144968 A1 May 25, 2017

Related U.S. Application Data

(62) Division of application No. 14/894,744, filed as application No. PCT/IN2014/000367 on May 30, 2014, now abandoned.

(30) Foreign Application Priority Data

May 30, 2013 (IN) .................. 1910/MUM/2013

(51) Int. Cl.
| | | |
|---|---|---|
| C07D 207/33 | (2006.01) | |
| C07D 207/333 | (2006.01) | |
| C07D 207/325 | (2006.01) | |
| A61K 31/402 | (2006.01) | |
| C07D 207/32 | (2006.01) | |

(52) U.S. Cl.
CPC ........ *C07D 207/333* (2013.01); *A61K 31/402* (2013.01); *C07D 207/32* (2013.01); *C07D 207/325* (2013.01)

(58) Field of Classification Search
None
See application file for complete search history.

(56) References Cited

U.S. PATENT DOCUMENTS

| | | |
|---|---|---|
| 4,231,938 A | 11/1980 | Monaghan et al. |
| 4,346,227 A | 8/1982 | Terahara et al. |
| 4,444,784 A | 4/1984 | Hoffman et al. |
| 5,273,995 A | 12/1993 | Roth |
| 5,354,772 A | 10/1994 | Kathawala |
| 6,166,063 A | 12/2000 | Villhauer |
| 6,395,767 B2 | 5/2002 | Robl et al. |
| 6,699,871 B2 | 3/2004 | Edmondson et al. |
| 6,987,123 B2 | 1/2006 | Lohray et al. |
| 7,041,837 B2 | 5/2006 | Lohray et al. |
| 7,323,491 B2 | 1/2008 | Lohray et al. |
| 7,407,955 B2 | 8/2008 | Himmelsbach et al. |
| 8,110,598 B2 | 2/2012 | Lohray et al. |
| 8,212,057 B2 | 7/2012 | Lohray et al. |
| 8,558,009 B2 | 10/2013 | Lohray et al. |
| 8,772,342 B2 | 7/2014 | Darteil et al. |
| 9,610,277 B2 | 4/2017 | Patel et al. |
| 9,656,954 B2 | 5/2017 | Jain et al. |
| 2003/0199498 A1 | 10/2003 | Lohray et al. |
| 2003/0236254 A1* | 12/2003 | Lohray .............. C07D 207/325 514/227.8 |
| 2007/0238776 A1 | 10/2007 | Lohray et al. |
| 2009/0196923 A1 | 8/2009 | Mandal et al. |
| 2011/0275669 A1 | 11/2011 | Lohray et al. |
| 2012/0121729 A1 | 5/2012 | Paterson et al. |
| 2013/0338209 A1 | 12/2013 | Gambhire et al. |
| 2016/0068484 A1 | 3/2016 | Jain et al. |
| 2016/0107989 A1 | 4/2016 | Dwivedi et al. |
| 2016/0136131 A1 | 5/2016 | Patel et al. |
| 2016/0166539 A1 | 6/2016 | Patel et al. |
| 2016/0194280 A1 | 7/2016 | Dwivedi et al. |
| 2016/0207884 A1 | 7/2016 | Dwivedi et al. |

FOREIGN PATENT DOCUMENTS

| | | |
|---|---|---|
| EP | 1586571 A1 | 10/2005 |
| IN | 1910/MUM/2013 | 12/2014 |
| WO | WO-91/19702 A1 | 12/1991 |

(Continued)

OTHER PUBLICATIONS

Ooi et al., Recent advances in asymmetric phase-transfer catalysis. Angewandte Chemie International Edition, 2007, 46, 4222-4266.*
Mastracchio, A. Phase-transfer catalysis. MacMillan Lab Group Meeting (power point presentation), Apr. 20, 2008, 1-53.*
Arnett et al., Solvent Effects in Organic Chemistry. V. Molecules, Ions, and Transition States in Aqueous Ethanol. Journal of American Chemical Society, 1965, 87, 1541-1553.*
International Search Report and Written Opinion dated Feb. 2, 2015 for International Patent Application No. PCT/IN2014/000367 (14 pages).
Jani, R. H. et al. "Pharmacokinetics, Safety, and Tolerability of Saroglitazar (ZYH1), a Predominantly PPARα Agonist with Moderate PPARγ Agonist Activity in Healthy Human Subjects" *Clin. Drug Investig.* (2013) vol. 33, pp. 809-816.
Brenna, E. et al. "Enzyme-mediated synthesis of EEHP and EMHP, useful pharmaceutical intermediates of PPAR agonists" *Tetrahedron: Asymmetry* (2009) vol. 20, pp. 2594-2599.

(Continued)

*Primary Examiner* — Po-Chih Chen
(74) *Attorney, Agent, or Firm* — Goodwin Procter LLP

(57) ABSTRACT

The present invention provides pyrroles having hypolipidemic hypocholesteremic activities. The invention provides saroglitazar and its pharmaceutically acceptable salts, hydrates, solvates, polymorphs or intermediates thereof. The invention also provides a process for the preparation of saroglitazar. The invention further provides intermediates as well process for preparation thereof.

6 Claims, 3 Drawing Sheets

(56) References Cited

FOREIGN PATENT DOCUMENTS

Figure 1:
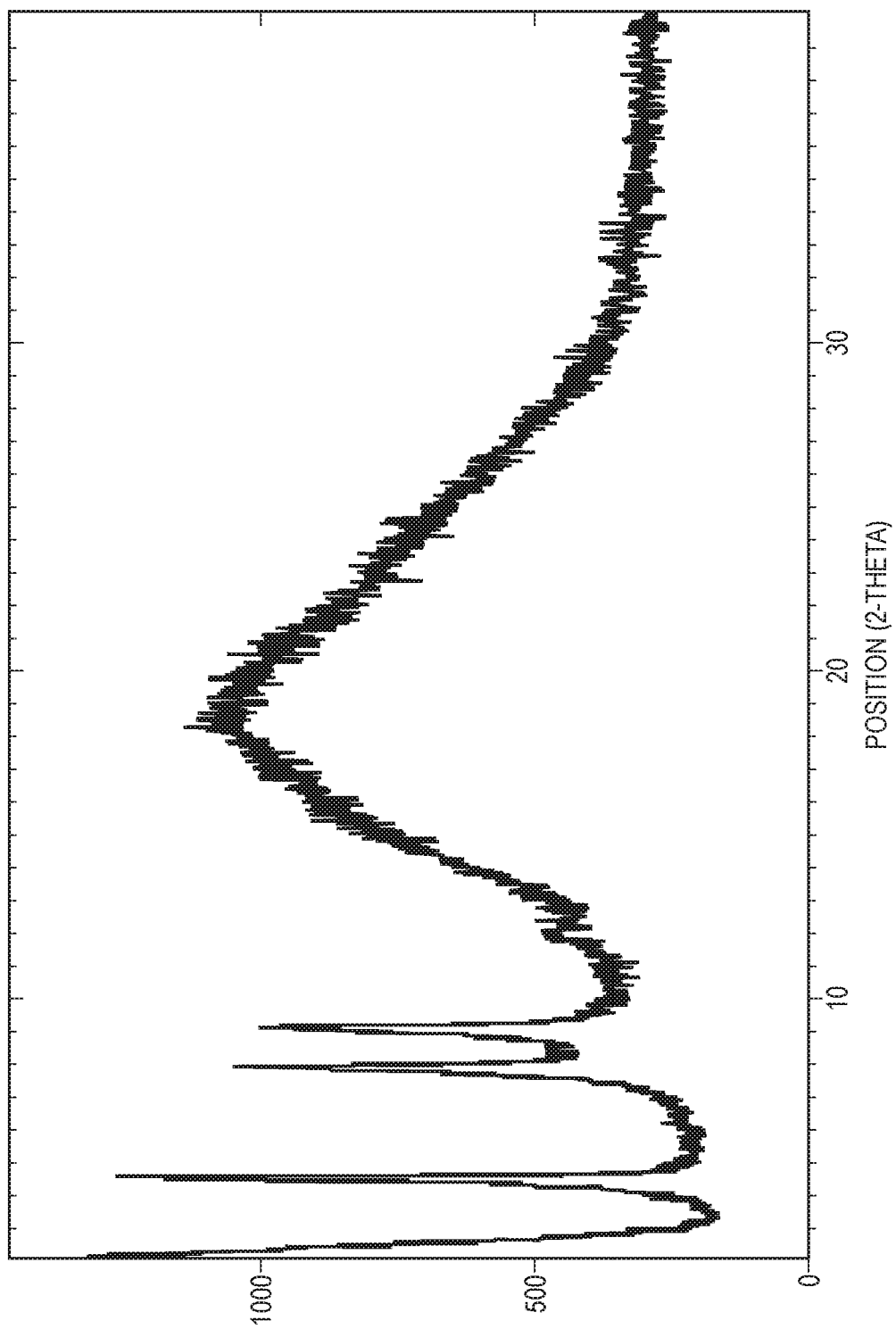

| WO | WO-94/01420 A1 | 1/1994 |
| --- | --- | --- |
| WO | WO-94/13650 A1 | 6/1994 |
| WO | WO-95/03038 A1 | 2/1995 |
| WO | WO-95/17394 A1 | 6/1995 |
| WO | WO-96/04260 A1 | 2/1996 |
| WO | WO-96/04261 A1 | 2/1996 |
| WO | WO-96/33998 A1 | 10/1996 |
| WO | WO-97/25042 A1 | 7/1997 |
| WO | WO-97/36579 A1 | 10/1997 |
| WO | WO-99/08501 A2 | 2/1999 |
| WO | WO-99/16758 A1 | 4/1999 |
| WO | WO-99/19313 A1 | 4/1999 |
| WO | WO-99/20614 A1 | 4/1999 |
| WO | WO-00/23417 A1 | 4/2000 |
| WO | WO-00/23445 A1 | 4/2000 |
| WO | WO-00/23451 A1 | 4/2000 |
| WO | WO-01/53257 A2 | 7/2001 |
| WO | WO-02/24625 A2 | 3/2002 |
| WO | WO-03/009841 A1 | 2/2003 |
| WO | WO-2005/031335 A1 | 4/2005 |
| WO | WO-2012/104869 A1 | 8/2012 |
| WO | WO-2014/174524 A1 | 10/2014 |
| WO | WO-2014/195967 A2 | 12/2014 |
| WO | WO-2015/001573 A1 | 1/2015 |
| WO | WO-2015/011730 A1 | 1/2015 |
| WO | WO-2015/029066 A1 | 3/2015 |
| WO | WO-2015/033357 A2 | 3/2015 |

OTHER PUBLICATIONS

International Preliminary Report on Patentability dated Dec. 1, 2015 for International Patent Application No. PCT/IN2014/000367 (9 pages).
International Search Report and Written Opinion dated Mar. 23, 2015 for Application No. PCT/IN2014/000584 (14 pages).
International Search Report and Written Opinion dated Dec. 19, 2014 for Application No. PCT/IN2014/000551 (11 pages).
Demuth, H.-U. et al. "Type 2 diabetes—Therapy with dipeptidyl peptidase IV inhibitors," *Biochim. Biophys. Acta*, 1751 (2005) pp. 33-44.
Augustyns, K. et al. "Inhibitors of proline-specific dipeptidyl peptidases: DPP IV inhibitors as a novel approach for the treatment of Type 2 diabetes," *Expert Opin. Ther. Patents*, (2005) vol. 15, No. 10, pp. 1387-1407.
Pai, V. et al. "A Multicenter, Prospective, Randomized, Double-blind Study to Evaluate the Safety and Efficacy of Saroglitazar 2 and 4 mg Compared to Pioglitazone 45 mg in Diabetic Dyslipidemia (PRESS V)." *J. Diabetes Sci. Technol.* (2014) vol. 8, No. 1, pp. 132-141.
Jani, R. H. et al. "A Multicenter, Prospective, Randomized, Double-Blind Study to Evaluate the Safety and Efficacy of Saroglitazar 2 and 4 mg Compared with Placebo in Type 2 Diabetes Mellitus Patients Having Hypertriglyceridemia Not Controlled with Atorvastatin Therapy (PRESS VI)," *Diabetes Technology & Therapeutics*, (2014) vol. 16, No. 2, pp. 63-71.
International Search Report and Written Opinion dated Dec. 23, 2014 for International Patent Application No. PCT/IN2014/000445 (10 pages).
International Preliminary Report on Patentability dated Oct. 6, 2015 for International Patent Application No. PCT/IN2014/000445 (7 pages).
Ansel et al. "Pharmaceutical Dosage Forms and Drug Delivery Systems, Seventh Edition" 1999, pp. 88-92.
Cairns, D. (editor) "Essentials of Pharmaceutical Chemistry, Fourth Edition" 2012, p. 14.
Bharate, S. et al. "Interactions and incompatibilities of pharmaceutical excipients with active pharmaceutical ingredients: a comprehensive review." *J. Excipient and Food Chem.* (2010) vol. 1, No. 3, pp. 3-26.

International Search Report and Written Opinion dated Nov. 20, 2014 for International Application No. PCT/IN2014/000489 (10 pages).
International Preliminary Report on Patentability dated Oct. 9, 2015 for International Application No. PCT/IN2014/000489 (7 pages).
Response to Written Opinion filed on May 21, 2015 for International Application No. PCT/IN2014/000489 (6 pages).
"Sodium Stearyl Fumarate", obtained on Jun. 23, 2015. Retrieved from the Internet: <URL: https://www.medicinescomplete.com/me/excipients/current/ . . . >, 4 pages.
Lieberman, et al. "Pharmaceutical Dosage Forms: Tablets, vol. 1, 2nd Edition" (1989) Marcel Dekker Inc., pp. 111-114.
Gennaro et al. "Remington's Pharmaceutical Sciences, 19th Edition" (1995) Mack Publishing, pp. 1380-1383.
Anonymous International Nonproprietary Names for Pharmaceutical Substances (INN); Jan. 1, 2012; Retrieved from the internet: URL: http://www.who.int/medicines/publications/druginformation/issues/PL_108.pdf; Retrieved on Oct. 15, 2013; pp. 401-471.
International Search Report and Written Opinion dated Nov. 20, 2013 for International Application No. PCT/IN2013/000391 (13 pages).
International Preliminary Report on Patentability dated Jul. 9, 2015 for International Application No. PCT/IN2013/000391 (9 pages).
IND Committee: "Minutes of IND Committee Meeting Held on Jul. 19, 2012" Retrieved on Oct. 15, 2013 from the Internet from URL: http://www.docstoc.com/docs/145152750/IND-Minutes-draft-19-07-12 (2 pages).
Anonymous "IND Minutes draft Jul. 19, 2012" Retrieved on Oct. 15, 2013 from the Internet from URL: http://www.docstoc.com/docs/145152750/IND-Minutes-draft-19-07-12 (1 page).
Anonymous "Lipaglyn™ Discovery, Development & Preclinical Studies" Retrieved on Oct. 15, 2013 from the Internet from URL: http://webcache.googleusercontent.com/search?q=cache:RGrhmY0HM3sJ:lipaglyn.com/downloads/Lipaglyn_Preclinical_Studies.ppsx (25 pages).
Jani, R. H. et al. "A Prospective Randomized, Double Blind, Placebo Controlled Study to Evaluate the Safety, Tolerability and Pharmacokinetics of ZYH1 Following Once a Day (OD) Oral Administrations up to 10 Days in Healthy Volunteers," *Diabetes* (2009) vol. 58, No. Suppl. 1, p. A569.
Ramirez, T. et al. "Structural Correlates of PPAR Agonist Rescue of Experimental Chronic Alcohol-Induced Steatohepatitis," *J. Clin. Exper. Pathology* (2012) vol. 2, No. 4, pp. 1-9.
Seo, Y. S. et al. "PPAR agonists treatment is effective in a nonalcoholic fatty liver disease animal model by modulating fatty-acid metabolic enzymes" *J. Gatroenterology Hepatology* (2008) vol. 23, No. 1, pp. 102-109.
Barb et al. (2016) "Pharmacological management of nonalcoholic fatty liver disease" Metabolism Clinical and Experimental 65:1183-1195.
Berger et al. (2005) "PPARs: Therapeutic targets for metabolic disease" Trends in Pharmacological Sciences 26(5): 244-251.
Chou et al. (2013) "Metrelepin: First Global Approval" Drugs 73:989-997.
Deeg et al. (2007) "Pioglitazone and Rosiglitazone Have Different Effects on Serum Lipoprotein Particle Concentrations and Sizes in Patients With Type 2 Diabetes and Dyslipidemia" Diabetes Care 30(10):2458-2464.
FDA News Release—FDA Approves Egrifta to treat Lipodystrophy in HIV Patients; downloaded from www.fda.gov/NewsEvents/Newsroom/PressAnnouncements/ucm233516.htm on Sep. 7, 2016 (2 pages).
Giri et al. "Efficacy of Saroglitazar, a Novel PPAR Agonist in a Mouse Model of Non-Alcoholic Steatohepatitis" Poster No. 2011, Keystone Symposia Conference, Mar. 22-27, 2015 at Whistler, British Colombia, Canada.
Jain et al. "Saroglitazar Shows Therapeutic Benefits in Mouse Model of Non-alcoholic Fatty Liver Disease (NAFLD) and Non-alcoholic Steatohepatitis (NASH)" Poster No. 1957-P, 75th Scientific Session—ADA, Jun. 5-9, 2015, Boston, MA, USA.
Package Insert for ACTOS (pioglitazone) tablets for oral use (2013).
Package Insert for AVANDIA (rosiglitazone maleate) Tablets (2008).

(56) References Cited

OTHER PUBLICATIONS

Palomer et al. (2016) "PPARβ/δ and lipid metabolism in the heart" Biochemica et Biophysica Acta 1861:1569-1578.
Yessoufou et al. (2010) "Multifaceted roles of peroxisome proliferator-activated receptors (PPARs) at the cellular and whole organism levels" Swiss Medical Weekly 140:w13071.
International Search Report dated May 9, 2012 for International Application No. PCT/IN2012/000069 (3 pages).
van Wijk, J. P. H. et al. "Comparison of Rosiglitazone and Metformin for Treating HIV Lipodystrophy: A Randomized Trial," *Ann. Internal Med.* (2005) vol. 143, No. 5, pp. 337-346.
Hadigan, C. et al. "Metabolic Effects of Rosiglitazone in HIV Lipodystrophy: A Randomized, Controlled Trial," *Ann. Internal Med.* (2004) vol. 140, No. 10, pp. 788-794. (Abstract Only).
Macallan, D. C. et al. "Treatment of Altered Body Composition in HIV Associated Lipodystrophy: Comparison of Rosiglitazone, Pravastatin, and Recombinant Human Growth Hormone," *HIV Clinical Trials*, (2008) vol. 9, Issue 4, pp. 254-268. (Abstract Only).
Tungsiripat, M. et al. "Rosiglitazone improves lipoatrophy in patients receiving thymidine-sparing regimens," *AIDS*, (2010) vol. 24, pp. 1291-1298.
Fan, W. and Evans, R. "PPARs and ERRs: molecular mediators of mitochondrial metabolism" *Curr. Opin. Cell Bio.* (2015) vol. 33, pp. 49-54.
LaBrecque, D. et al. "World Gastroenterology Organisation, Global Guidelines: Nonalcoholic Fatty Liver disease and Nonalcoholic Steatohepatitis (long version)" World Gastroenterology Organisation (2012) 29 pages.
International Preliminary Report on Patentability dated Aug. 15, 2013 for International Application No. PCT/IN2012/000069 (5 pages).
International Preliminary Report on Patentability dated Mar. 1, 2016 for Application No. PCT/IN2014/000551 (7 pages).
International Preliminary Report on Patentability dated Mar. 8, 2016 for International Patent Application No. PCT/IN2014/000584 (10 pages).
Written Opinion of the International Searching Authority dated May 9, 2012 for International Application No. PCT/IN2012/000069 (4 pages).
Pharmatrans Sanaq AG "LubriSanaq" Dated Feb. 5, 2008. (2 pages).
Lemoine, M. et al. "Steatohepatitis (fatty liver) Is Associated With Increased Hepatic Expression of SREBP-1 In HIV-Infected Patients With Antiretroviral Therapy-Linked Lipodystrophy," Abstract from 55th Annual Meeting of the American Association for the Study of Liver Diseases, Oct. 29 to Nov. 2, 2004; Printed from http://www.natap.org/2004/AASLD/aasld_10.htm. (8 pages).
Bugianesi, E. et al. "Insulin Resistance: A Metabolic Pathway to Chronic Liver Disease," *Hepatology* (2005) vol. 42, No. 5, pp. 987-1000.
Angulo, P. "GI Epidemiology: nonalcoholic fatty liver disease," *Aliment. Pharmacol. Ther.* (2007) vol. 25, No. 8, pp. 883-889.
Acdisol Product Overview (year 2005).
USPTO Trademark Database Entry for AEROSIL.
Boulet, L-P. "Influence of Comorbid Conditions on Asthma" *European Respiratory Journal* (2009) vol. 33, pp. 897-906.
Chatila et al. "Comorbidities in Chronic Obstructive Pulmonary Disease" *Proc. Am. Thorac. Soc.* (2008) vol. 5, pp. 549-555.
Jackson, K. "No Benefit from Ezetimibe in NASH" in Medpage Today (Jun. 2015).
Prescribing Information for Zetia® (ezetimibe; year 2012).
Rakoski, M. et al. "Meta-analysis: Insulin Sensitizers for the Treatment of Non-alcoholic Steatohepatitis" *Aliment. Pharmacol. Ther.* (2010) vol. 32, pp. 1211-1221.

\* cited by examiner

PROCESS FOR PREPARATION OF PYRROLES HAVING HYPOLIPIDEMIC HYPOCHOLESTEREMIC ACTIVITIES

CROSS-REFERENCE TO RELATED APPLICATIONS

This application is a divisional of U.S. patent application Ser. No. 14/894,744, filed Nov. 30, 2015, which is the national stage of International (PCT) Patent Application No. PCT/IN2014/000367, filed May 30, 2014, which claims the benefit of and priority to Indian Patent Application No. 1910/MUM/2013, filed May 30, 2013.

FIELD OF THE INVENTION

The present invention relates to a process for the preparation of pyrroles having hypolipidemic hypocholesteremic activities. In particular, the invention relates to a process for the preparation of saroglitazar and its pharmaceutically acceptable salts, hydrates, solvates, polymorphs or intermediates thereof. The invention also relates to a pharmaceutical composition comprising saroglitazar and its pharmaceutically acceptable salts together with one or more pharmaceutically acceptable carriers, excipients or diluents.

BACKGROUND OF THE INVENTION

The following discussion of the prior art is intended to present the invention in an appropriate technical context and allow its significance to be properly appreciated. Unless clearly indicated to the contrary, however, reference to any prior art in this specification should be construed as an admission that such art is widely known or forms part of common general knowledge in the field.

Pyrrole derivative of present invention is chemically, (2S)-2-ethoxy-3-[4-(2-(2-methyl-5-[4-(methylsulfanyl)phenyl]-1H-pyrrol-1-yl)ethoxy)phenyl]propanoic acid, which may be optically active or racemic and its pharmaceutically acceptable salts, hydrates, solvates or polymorphs thereof. The INN name for pyrrole derivative is Saroglitazar® which is magnesium salt of pyrrole compound of Formula (I), having below chemical structure.

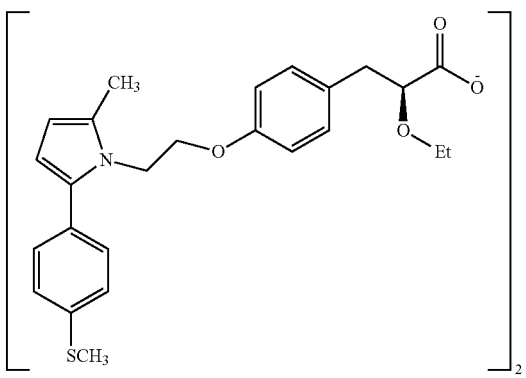

(I)

The compound of Formula (I) lower or modulate triglyceride levels and/or cholesterol levels and/or lower density lipoproteins (LDL) and raise HDL plasma levels and hence are useful in combating different medical conditions, where such lowering (and raising) is beneficial. Thus, it could be used in the treatment and/or prophylaxis of obesity, hyperlipidemia, hypercholesteremia, hypertension, atherosclerotic disease events, vascular restenosis, diabetes and many other related conditions. The compound of Formula (I) are useful to prevent or reduce the risk of developing atherosclerosis, which leads to diseases and conditions selected from arteriosclerotic cardiovascular diseases, stroke, coronary heart diseases, cerebrovascular diseases, peripheral vessel diseases and related disorders.

U.S. Pat. No. 6,987,123 B2 (the US '123 Patent) discloses novel heterocyclic compounds, their preparation, pharmaceutical compositions containing them and their use in medicine. The US '123 patent discloses five reaction pathways for the synthesis of pyrrole derivatives.

In route-1 the compound of Formula (1a) and (1b) are reacted under Paal-Knorr conditions to obtain compound (1) as shown below:

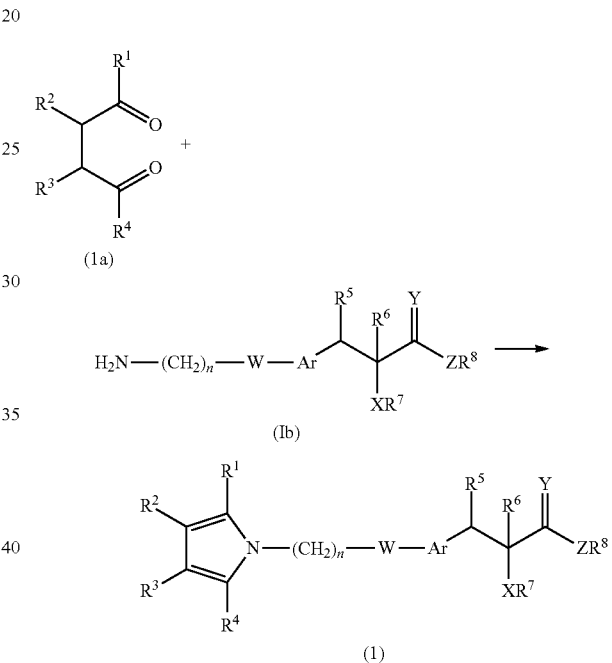

In route-2 the compound of Formula (1c) and (1d) are reacted in presence of base in organic solvent to obtain the compound (1) as shown below:

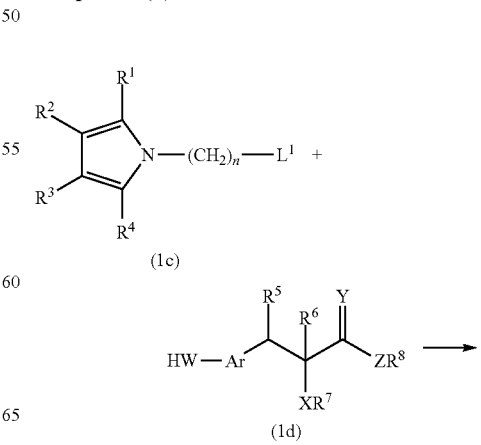

-continued

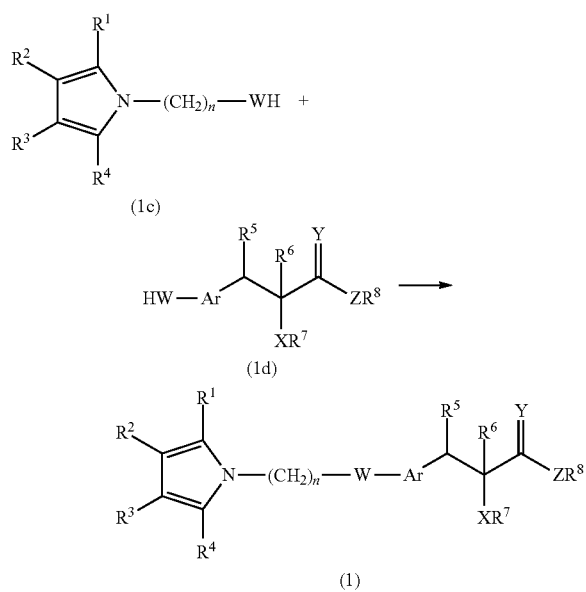

In route-3 the compound of Formula (1e) and (1d) are reacted in presence of coupling agents like DCC, EDC etc. to obtain the compound (1) as shown below:

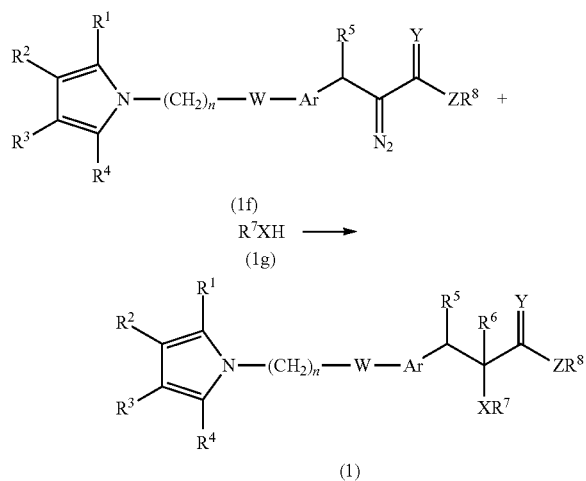

In route-4 the compound of Formula (1f) and (1g) are reacted in presence of rhodium salts selected from rhodium (II) acetate in organic solvent like benzene, toluene, ether, THF, dioxane to obtain the compound (1) as shown below:

In route-5 the compound of Formula (1e) and (1d) are reacted under Wittig Horner conditions to obtain the compound (1) as shown below:

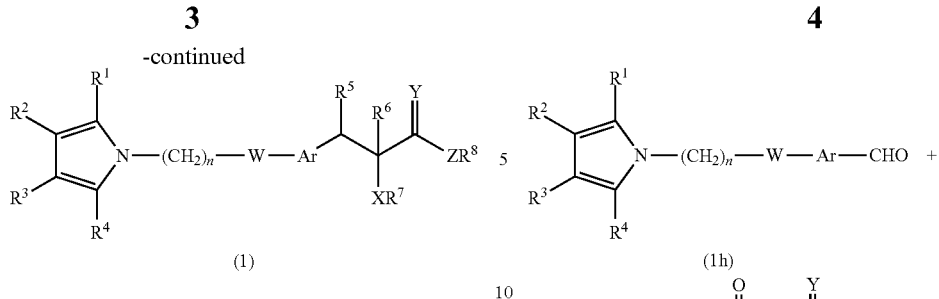

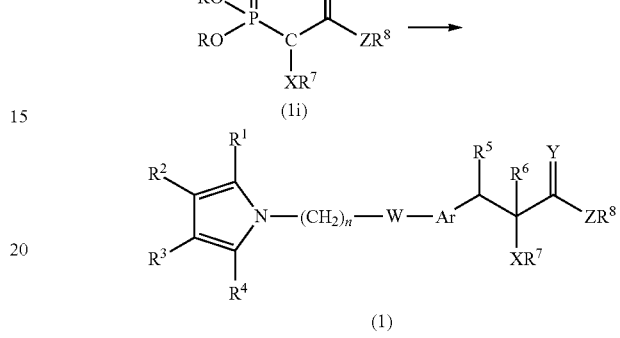

U.S. Pat. Nos. 7,041,837 B2, 7,323,491 B2, 8,110,598 B2, 8,212,057 B2 discloses different pyrrole derivative of Formula (1) and their intermediates.

U.S. PG-Pub. No. 2011/0275669 A1 discloses the process for the preparation of pyrrole derivative of general Formula (1) prepared by the five reaction pathways as disclosed herein above.

International (PCT) publication WO 2012/104869 A1 provides the use of compound of Formula (1) for the treatment of lipodystrophy.

The different physical properties exhibited by polymorphs affect important pharmaceutical parameters selected from storage, stability, compressibility, density and dissolution rates (important in determining bioavailability). Stability differences may result from changes in chemical reactivity (e.g., differential hydrolysis or oxidation, such that a dosage form discolors more rapidly when comprised of one polymorph than when comprised of another polymorph), mechanical changes (e.g., tablets crumble on storage as a kinetically favored crystalline form converts to thermodynamically more stable crystalline form) or both (e.g., tablets of one polymorph are more susceptible to breakdown at high humidity). Solubility differences between polymorphs may, in extreme situations, result in transitions to crystalline forms that lack potency or are toxic. In addition, the physical properties of the crystalline form to that of an amorphous form may be important in pharmaceutical processing. For example, an amorphous form may provide better bioavailability than the crystalline form. Thus, a present amorphous form may be useful for formulations which can have better stability, solubility, storage, compressibility etc important for formulation and product manufacturing and doesn't degrade to crystalline forms of saroglitazar.

Therefore, it is desirable to have amorphous forms of drugs with high purity to meet the regulatory requirements and also highly reproducible processes for their preparation.

In view of the above, it is therefore, desirable to provide an efficient, more economical, less hazardous and eco-friendly process for the preparation of saroglitazar.

SUMMARY OF THE INVENTION

In one aspect, there is provided a substantially amorphous form of saroglitazar magnesium of Formula (I)

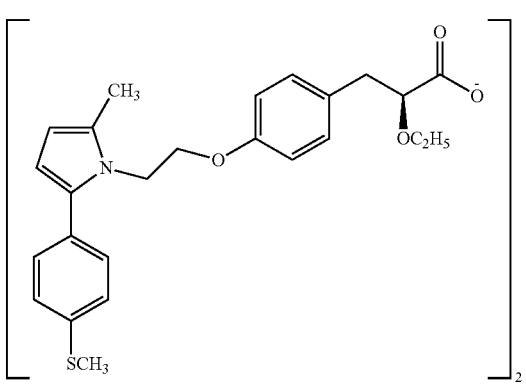

(I)

In another aspect, there is provided a process for the preparation saroglitazar of Formula (IA) or its pharmaceutically acceptable salt,

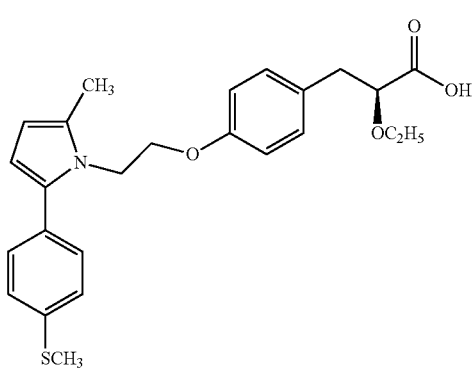

(IA)

the process comprising:
(a) reacting hydroxy compound (A) with the compound (A1') in one or more organic solvents in presence of a base and a phase transfer catalyst to obtain alkoxy ester compound of Formula (II);

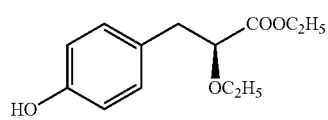

(A)

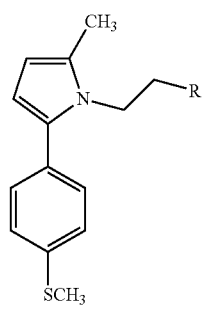

(A1')

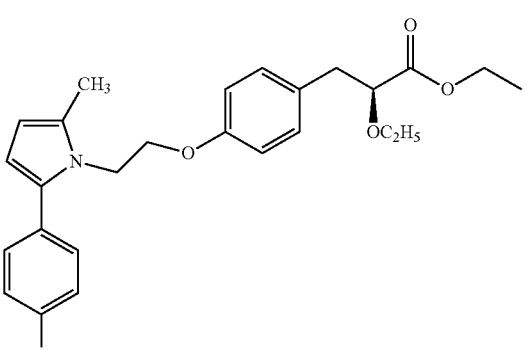

(II)

wherein, R is selected from mesylate, tosylate, triflate;
(b) hydrolyzing alkoxy ester compound of Formula (II) with a base to obtain saroglitazar; and
(c) optionally, converting the saroglitazar to its pharmaceutically acceptable salt.

In another aspect, there is provided a process for the preparation of saroglitazar magnesium of Formula (I),

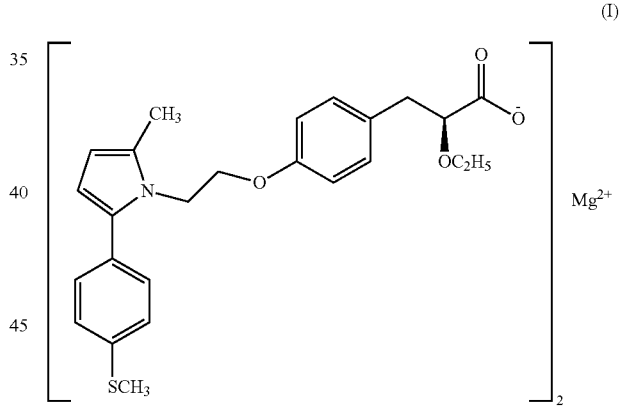

(I)

the process comprising:
(a) reacting hydroxy compound (A) with a mesylate compound (A1) in one or more organic solvents in the presence of a base and a phase transfer catalyst to obtain alkoxy ester compound of Formula (II);

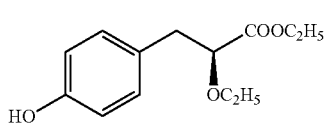

(A)

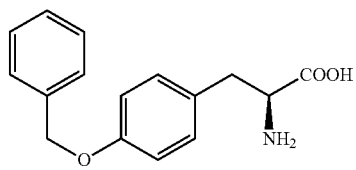
(A1)

(c) diazotization of the compound (D) in the presence of sodium nitrite and an acid followed by hydrolysis with water to obtain compound (C);

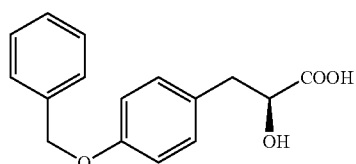
(C)

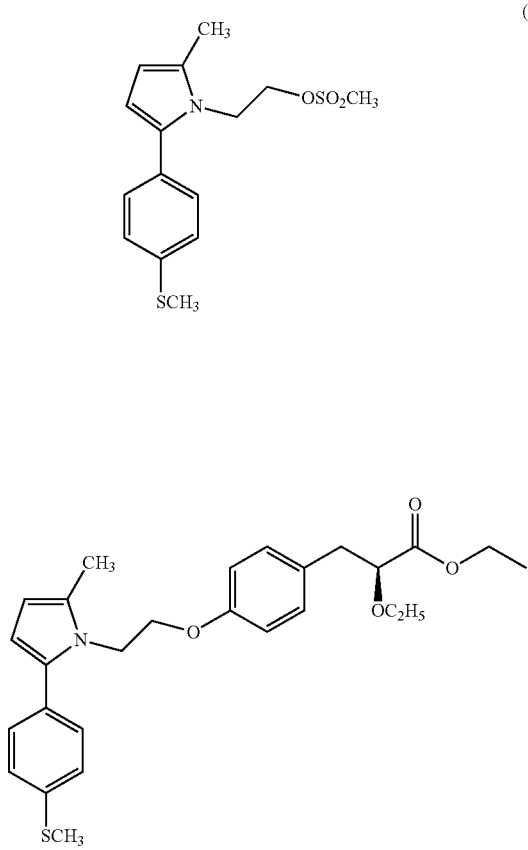
(II)

(d) reacting the compound (C) with diethyl sulfate in one or more organic solvents in presence of a base and a phase transfer catalyst to obtain compound (B); and

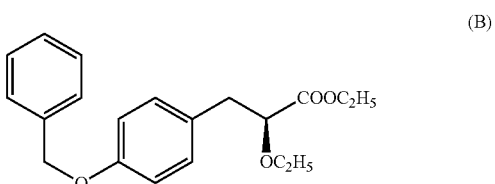
(B)

(b) hydrolyzing the alkoxy ester compound of Formula (II) with a base to obtain saroglitazar; and (c) reacting the saroglitazar with a magnesium source to obtain saroglitazar magnesium of Formula (I).

(e) deprotecting the compound (B) to obtain hydroxy compound (A).

In still another aspect, there is provided a process for the preparation of hydroxy compound of Formula (A), In another aspect, there is provided a process for the preparation of mesylate compound of Formula (A1),

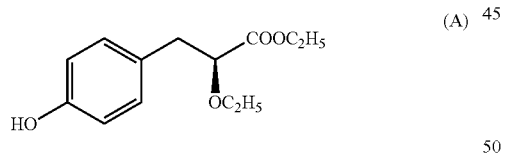
(A)

the process comprising:

(a) reacting L-tyrosine (E) with cupric sulphate pentahydrate in the presence of a base to obtain copper complex of L-tyrosine;

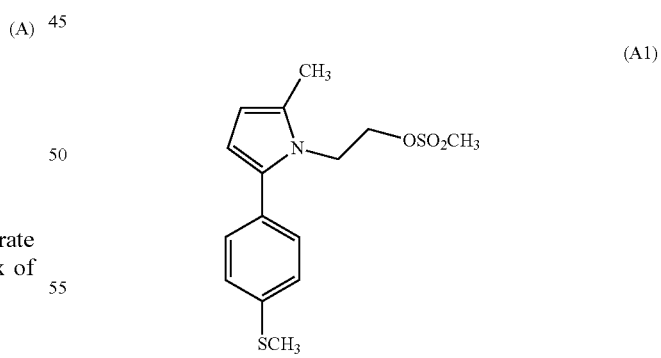
(A1)

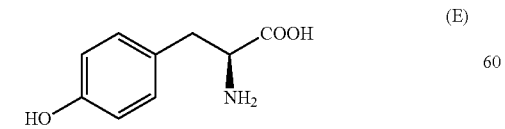
(E)

(b) reacting the copper complex of L-tyrosine with benzyl halide in the presence of a base followed by hydrolysis to obtain compound (D);

the process comprising:

(a) reacting 2-bromo-1-(4-(methylthio)phenyl)ethanone (E1) with methyl acetoacetate in one or more organic solvents in the presence of a base to obtain compound (D1);

(E1)

[structure: 4-(methylthio)phenacyl bromide]

(D1)

[structure: dimethyl 2-(2-(4-(methylthio)phenyl)-2-oxoethyl)malonate-like]

(b) hydrolyzing the compound (D1) with a base followed by decarboxylation to obtain compound (C1);

(C1)

[structure: 1-(4-(methylthio)phenyl)pentane-1,4-dione]

(c) reacting the compound (C1) with ethanolamine under Paal-Knorr conditions in the presence of an acid to obtain compound (B1); and (B1)

[structure: 2-(2-methyl-5-(4-(methylthio)phenyl)-1H-pyrrol-1-yl)ethanol]

(d) reacting the compound (B1) with methane sulphonyl chloride in the presence of a base in one or more organic solvents to obtain the mesylate compound (A1).

In yet another aspect, there is provided substantially amorphous form of saroglitazar magnesium having particle size distributions having D(10) of about 10 μm or less, D(50) of about 25 μm or less, and D(90) of about 100 μm or less or any combination thereof.

In another aspect, there is provided saroglitazar magnesium having a purity of at least about 98% by area percentage of HPLC. In particular, saroglitazar magnesium having a purity of at least about 99%, more particularly, a purity of at least about 99.5%, further more particularly, a purity of at least about 99.8%, most particularly, a purity of at least about 99.9% by area percentage of HPLC.

In another aspect, there is provided saroglitazar magnesium having a chiral purity of at least about 98% by area percentage of HPLC. In particular, saroglitazar magnesium having a chiral purity of at least about 99%, more particularly, a chiral purity of at least about 99.5%, further more particularly, a chiral purity of at least about 99.8%, most particularly, a chiral purity of at least about 99.9% by area percentage of HPLC.

In another aspect, there is provided a pharmaceutical composition comprising an amorphous form of saroglitazar magnesium together with one or more pharmaceutically acceptable carriers, excipients or diluents.

BRIEF DESCRIPTION OF THE ACCOMPANYING DRAWINGS

Figure 2:
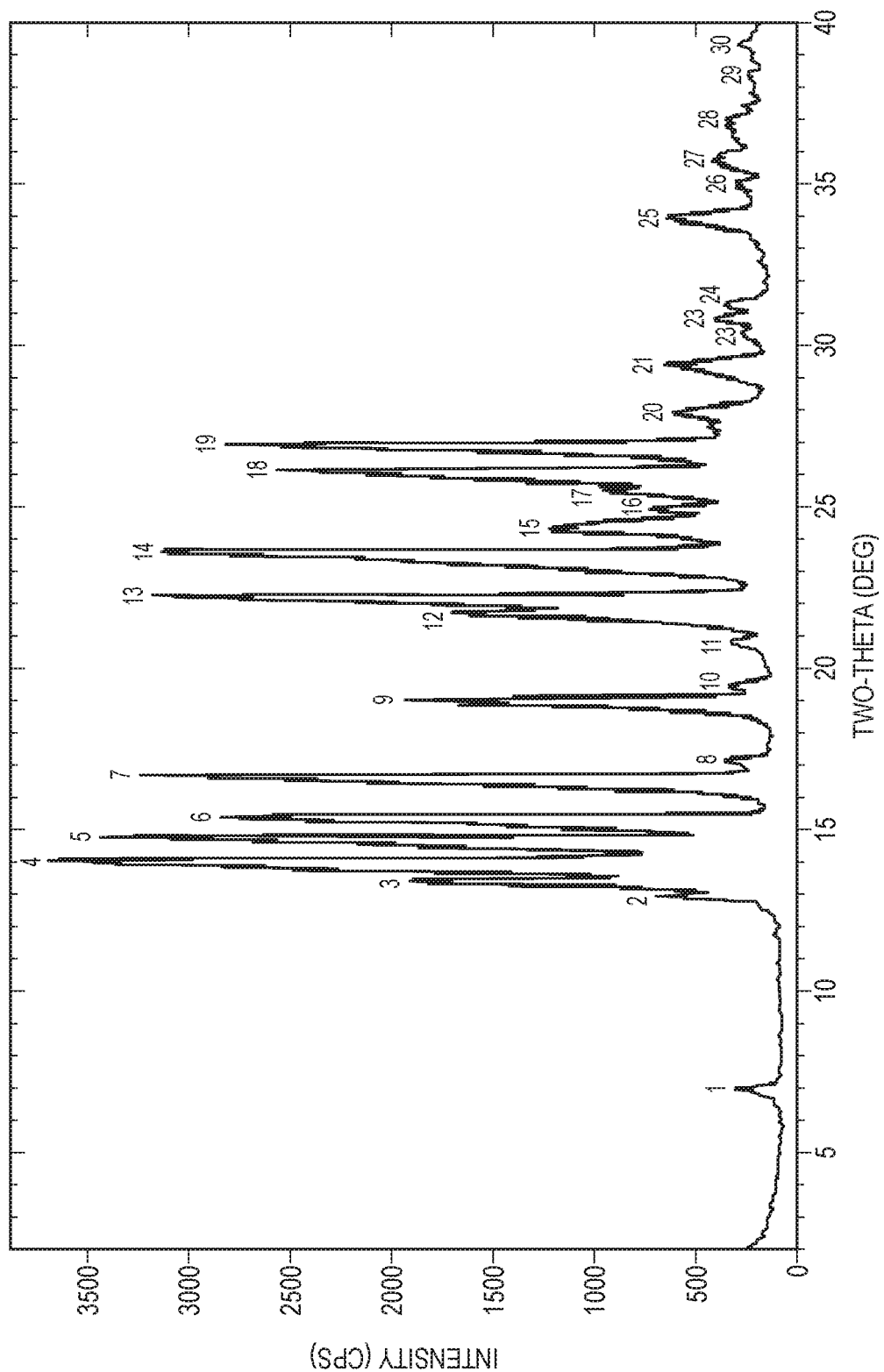

FIG. 1 discloses the X-ray diffractogram (XRD) of substantially amorphous form of saroglitazar magnesium of Formula (I);

FIG. 2 discloses the X-ray diffractogram (XRD) of hydroxy compound (A); and

Figure 3:
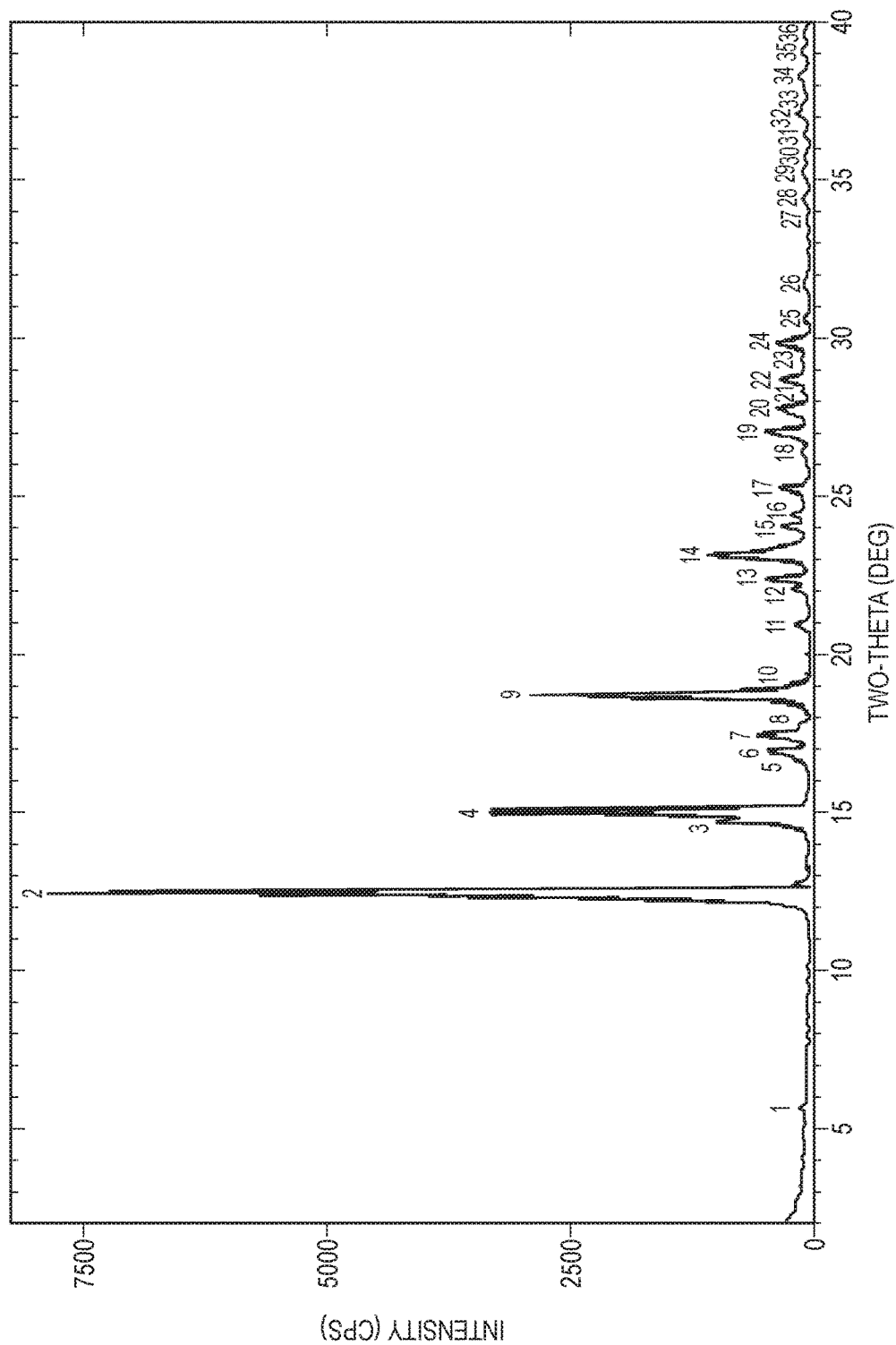

FIG. 3 discloses the X-ray diffractogram (XRD) of mesylate compound (A1).

DETAILED DESCRIPTION OF THE INVENTION

The above and other objects of the present invention are achieved by the process of the present invention, which leads to substantially amorphous form of saroglitazar magnesium suitable for pharmaceutical use.

Optionally, the solution, prior to any solids formation, can be filtered to remove any undissolved solids, solid impurities prior to removal of the solvent. Any filtration system and filtration techniques known in the art can be used.

All ranges recited herein include the endpoints, including those that recite a range "between" two values. Terms selected from "about", "generally", "substantially," are to be construed as modifying a term or value such that it is not an absolute. This includes, at least the degree of expected experimental error, technique error and instrument error for a given technique used to measure a value.

The term "substantially amorphous" herein means amorphous saroglitazar magnesium having less than about 25% of crystalline saroglitazar magnesium.

The terms herein below are interchangeable and used in the description.

"DMF" refers to N,N-dimethylforamide
"DMAc" refers to N,N-dimethylacetamide
"DMSO" refers to N,N-dimethylsulfoxide
"NMP" refers to N-methylpyrrolidone
"THF" refers to tetrahydrofuran
"MTBE" refers to methyl tert-butyl ether
"TEA" refers to triethylamine
"TBA" refers to tert-butyl amine
"DIPA" refers to diisopropyl amine
"DIPEA" refers to diisopropyl ethylamine
"DBU" refers to 1,8-diazabicyclo[5.4.0]undec-7-ene
"DABCO" refers to 1,4-diazabicyclo[2.2.2]octane
"DBN" refers to 1,5-diazabicyclo[4.3.0]non-5-ene
"HPLC" refers to high performance liquid chromatography In one general aspect, there is provided a substantially amorphous form of saroglitazar magnesium of Formula (I).

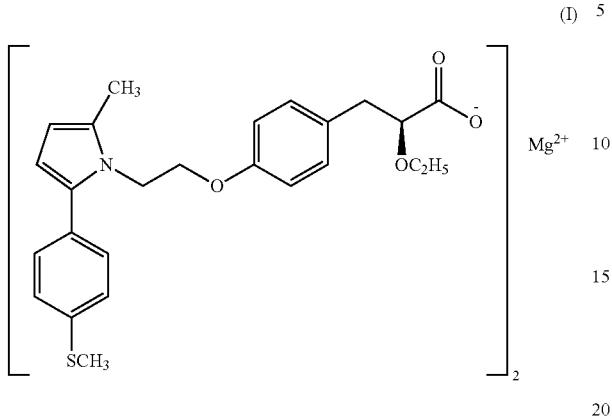

In another general aspect, there is provided a substantially amorphous form of saroglitazar magnesium having a purity of at least about 98% by area percentage of HPLC and less than about 0.5% residual solvent.

In another general aspect, there is provided substantially amorphous form of saroglitazar magnesium having an X-ray powder diffraction pattern substantially the same as that shown in FIG. 1 or by X-ray powder diffraction pattern having characteristic peaks expressed in degress 2θ (±0.2° 2θ) at 4.5°, 7.9° and 9.0°±0.2° 2θ.

In general, the substantially amorphous form of saroglitazar magnesium is substantially free from residual solvents. The term "substantially free" means residual solvents within the permissible ICH limits suitable for pharmaceutical preparations. For example but not limited to less than about 0.5%, particularly less than about 0.3% or more particularly less than about 0.2% by GC.

In another general aspect, there is provided a process for the preparation saroglitazar of Formula (IA) or its pharmaceutically acceptable salt,

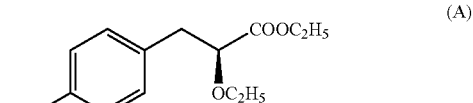

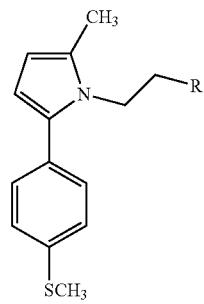

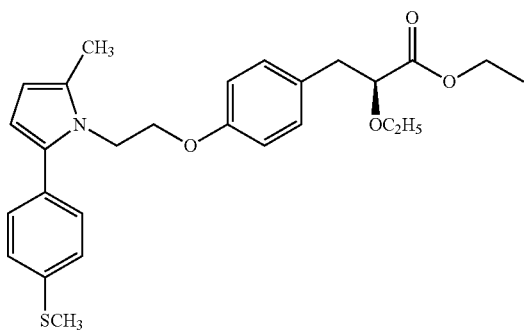

wherein, R is selected from mesylate, tosylate, triflate;

(b) hydrolyzing the alkoxy ester compound of Formula (II) with a base to obtain saroglitazar; and (c) optionally, converting the saroglitazar to its pharmaceutically acceptable salt.

In another general aspect, there is provided a process for the preparation saroglitazar magnesium of Formula (I),

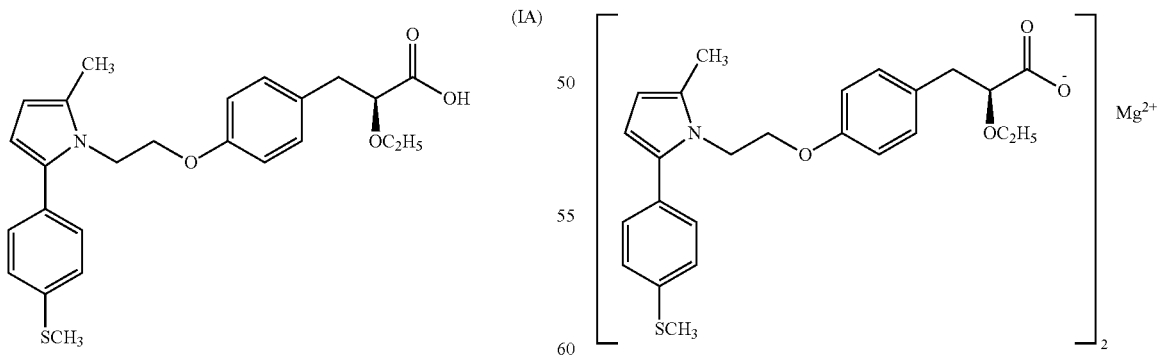

the process comprising:
(a) reacting hydroxy compound (A) with a compound (A1') in one or more organic solvents in the presence of a base and a phase transfer catalyst to obtain alkoxy ester compound of Formula (II);

the process comprising:
(a) reacting hydroxy compound (A) with a mesylate compound (A1) in one or more organic solvents in the presence of a base and a phase transfer catalyst to obtain alkoxy ester compound of Formula (II);

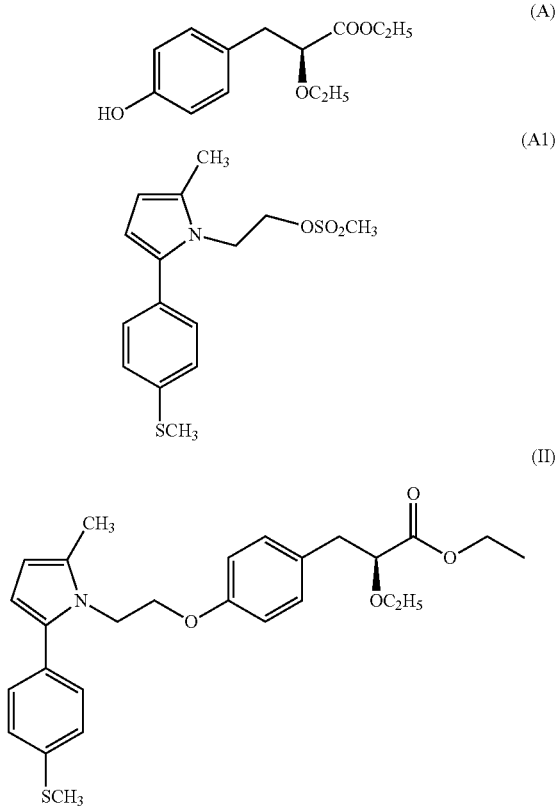

(b) hydrolyzing the alkoxy ester compound of Formula (II) with a base to obtain saroglitazar; and
(c) reacting the saroglitazar with a magnesium source to obtain saroglitazar magnesium of Formula (I).

In general, the organic solvent comprises one or more of alcohols selected from methanol, ethanol, isopropanol, 2-propanol, 1-butanol, and t-butyl alcohol; ketones selected from acetone, butanone, and methyl isobutyl ketone; esters selected from ethyl acetate, isopropyl acetate, t-butyl acetate, and isobutyl acetate; chlorinated hydrocarbons selected from methylene dichloride, ethylene dichloride, and chlorobenzene; hydrocarbons selected from pentane, hexane, heptane, and cyclohexane; ethers selected from tetrahydrofuran, 1,4-dioxane, diisopropyl ether, diethyl ether, and methyl tert-butyl ether; or mixture thereof. In particular, mixture of cyclohexane and tetrahydrofuran may be used.

The base comprises one or more of sodium hydroxide, potassium hydroxide, lithium hydroxide, calcium hydroxide, sodium carbonate, potassium carbonate, sodium bicarbonate, potassium bicarbonate, sodium hydride, potassium hydride, potassium tert-butoxide, and sodium pentoxide. In particular, potassium carbonate may be used. The base may be preferably anhydrous.

The phase transfer catalyst comprises one or more of tetrabutyl ammonium bromide (TBAB), tetrabutyl ammonium iodide (TBAI), benzyl triethyl ammonium chloride (TEBAC), polyethylene Glycol (PEG-200, 400, 600, 800, 1000), crown ethers selected from 12-crown-4, 15-crown-5, 18-crown-6, dibenzo-18-crown-6, and diaza-18-crown-6. In particular, the phase transfer catalyst may be 18-crown-6.

In general, the reaction of hydroxy compound (A) with a mesylate compound (A1) may be performed under heating at 35° C. to about reflux temperature of solvents. In particular, the reaction may be heated at 75° C. to 85° C. till the completion of the reaction. The reaction may be heated for about 25 hours to about 40 hours. In particular, for about 36 hours.

In another general aspect, the obtained alkoxy ester (II) may be proceeded further without isolating. Therefore, the alkoxy ester (II) may be further hydrolyzed in-situ.

The base for hydrolyzing alkoxy ester (II) comprises one or more of sodium hydroxide, potassium hydroxide, lithium hydroxide, calcium hydroxide, sodium carbonate, potassium carbonate, sodium bicarbonate, potassium bicarbonate, sodium hydride, and potassium hydride. In particular, sodium hydroxide may be used.

In general, the magnesium source comprises one or more of magnesium hydroxide, magnesium methoxide and magnesium acetate. In particular, the magnesium source may be magnesium acetate tetrahydrate.

In general, the compound of Formula (I) may be obtained by extracting the reaction mixture with one or more organic solvents followed by washing the organic layer and removal of the organic solvents. The residue may be treated with same solvents and added into an anti-solvent to obtain compound of Formula (I).

The product thus obtained may be filtered and dried under vacuum tray drier, sieved and milled to obtain particle size distribution. The milled product may be further dried till constant weight may be obtained to obtain saroglitazar magnesium substantially free from residual solvents.

The organic solvent used for extraction comprises one or more of esters selected from ethyl acetate, isopropyl acetate, t-butyl acetate, and isobutyl acetate; chlorinated hydrocarbons selected from methylene dichloride, ethylene dichloride, and chlorobenzene; aromatic hydrocarbons selected from toluene, xylene, and ethylbenzene.

The anti-solvent comprises one or more of aliphatic hydrocarbons selected from pentane, hexane, heptane, and cyclohexane; ethers like tetrahydrofuran, 1,4-dioxane, diisopropyl ether, diethyl ether, and methyl tertbutyl ether. In particular, the anti-solvent may be n-heptane.

The product may be obtained by removal of anti-solvent by the known technique in the art comprises one or more of filtration, centrifugation, decantation, rotational distillation using device selected from Buchi Rotavapor, spray dyring, agitated thin film drying ("ATFD"), and freeze drying (lyophilization); or any other know techniques.

In general, the sieving of product may be done through 0.5 sieve followed by milling. Examples of such milling include various makes of ball mills, roller mills, gyratory mills, multi-mills, Jet-mills. In a preferred aspect, a mill selected from a Micros Super Fine Mill (available from Nara Machinery Co. Ltd or Tokyo, Japan), Multi-Mill Sr. No. G. 1.132 (available from Grooves International Pharmaceutical & Chemical Machinery), Jet-Mill from Midas Micronizer M-100 Aerosol (No. 154/07-08 (available from microtech Engineering Company) or a common mixer grinder can be used. Alternatively another commercially available milling machine can be used.

In another general aspect, there is provided substantially amorphous form of saroglitazar magnesium having a particle size distribution having D(10) of about 50 µm or less, D(50) of about 200 µm or less and D(90) of about 400 µm or less; or any combination thereof. In particular, there is provided substantially amorphous form of saroglitazar magnesium having a particle size distribution having D(10) of about 10 µm or less, D(50) of about 25 µm or less and D(90) of about 100 µm or less.

In another general aspect, there is provided saroglitazar magnesium having a purity of at least about 98% by area percentage of HPLC. In particular, saroglitazar magnesium having a purity of at least about 99%, more particularly, a purity of at least about 99.5%, further more particularly, a purity of at least about 99.8%, most particularly, a purity of at least about 99.9% by area percentage of HPLC.

In another general aspect, there is provided saroglitazar magnesium having a chiral purity of at least about 98% by area percentage of HPLC. In particular, saroglitazar magnesium having a chiral purity of at least about 99%, more particularly, a chiral purity of at least about 99.5%, further more particularly, a chiral purity of at least about 99.8%, most particularly, a chiral purity of at least about 99.9% by area percentage of HPLC.

In another general aspect, there is provided a process for the preparation of hydroxy compound of Formula (A),

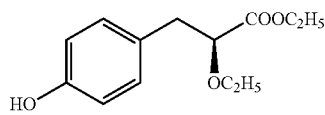

(A)

the process comprising:

(a) reacting L-tyrosine (E) with cupric sulphate pentahydrate in the presence of a base to obtain copper complex of L-tyrosine;

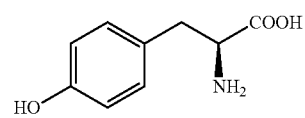

(E)

(b) reacting the copper complex of L-tyrosine with benzyl halide in the presence of a base followed by hydrolysis to obtain compound (D);

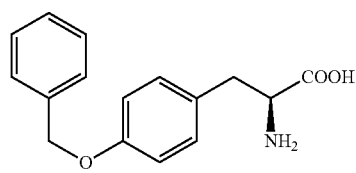 [SMILES: N[C@@H](Cc1ccc(OCc2ccccc2)cc1)C(=O)O]

(D)

(c) diazotization of the compound (D) in the presence of sodium nitrite and an acid followed by hydrolysis with water to obtain compound (C);

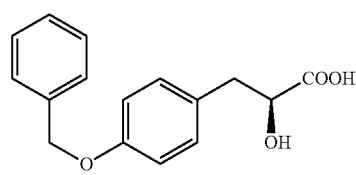

(C)

(d) reacting the compound (C) with diethyl sulfate in one or more organic solvents in the presence of a base and a phase transfer catalyst to obtain compound (B); and

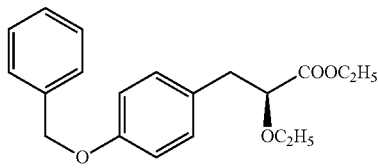

(B)

(e) deprotecting the compound (B) to obtain hydroxy compound (A).

In general, the base in step (a) comprises one or more of sodium hydroxide, potassium hydroxide, lithium hydroxide, calcium hydroxide, sodium carbonate, potassium carbonate, sodium bicarbonate, potassium bicarbonate, sodium hydroxide, and potassium hydride. In particular, aqueous sodium hydroxide solution may be used.

The reaction mixture comprising L-tyrosine, cupric sulphate pentahydrate and aqueous sodium hydroxide may be heated from about 40° C. to reflux temperature of water. In particular, the reaction mixture may be heated at about 100° C. to about 102° C. for about 1 hour and cooled to about 20° C. to about 25° C. The reaction mixture may be further diluted with one or more of organic solvents.

The organic solvent comprises one or more of alcohols selected from methanol, ethanol, isopropanol, 2-propanol, 1-butanol, and t-butyl alcohol; ketones selected from acetone, butanone, and methyl isobutyl ketone; esters selected from ethyl acetate, isopropyl acetate, t-butyl acetate, and isobutyl acetate. In particular, methanol may be used.

The copper complex of L-tyrosine solution may be treated with benzyl halide in the presence of a base. The base comprises same or different from the one used herein before. In particular, sodium hydroxide may be used. The benzyl halide comprises one or more of benzyl chloride or benzyl bromide. In particular, benzyl bromide may be used.

The reaction mixture may be further heated from about 40° C. to about reflux temperature of solvent. In particular, the reaction mixture may be heated from about 60° C. to about 65° C. The benzyl protected L-tyrosine copper complex may be isolated by the known methods as described herein above. The complex may be hydrolyzed with an acid to obtain compound (D).

The acid comprises one or more of acetic acid, hydrochloric acid, sulfuric acid, formic acid, hydrobromic acid, and trifluoroacetic acid. In particular, hydrochloric acid may be used.

The compound (D) obtained in step (b) may be diazotized with sodium nitrite in presence of an acid. The acid comprises one or more of hydrochloric acid, sulfuric acid, hydrobromic acid, and nitric acid. In particular sulfuric acid may be used.

The diazotization may be performed in organic solvents comprises one or more of alcohols selected from methanol, ethanol, isopropanol, 2-propanol, 1-butanol, and t-butyl alcohol; ketones selected from acetone, butanone, and methylisobutyl ketone; esters selected from ethyl acetate, isopropyl acetate, t-butyl acetate, and isobutyl acetate; polar aprotic solvents selected from N,N-dimethylforamide, N,N-dimethylacetamide, N-methylpyrrolidone, and N,N-dimethylsulfoxide; or mixtures thereof. In particular, N,N-dimethylsulfoxide may be used.

The compound (C) may be obtained by usual work-up procedure in one or more organic solvents or mixture thereof. The organic solvent comprises mixture of ethyl acetate and water.

In general, the organic solvent for step (d) comprises one or more of esters selected from ethyl acetate, isopropyl acetate, t-butyl acetate, and isobutyl acetate; hydrocarbons selected from toluene, xylene, ethyl benzene, heptane, hexane, and cyclohexane; chlorinated solvents selected from methylene dichloride, ethylene dichloride, chlorobenzene, chloroform, and carbontetrachloride. In particular, toluene may be used.

In general, the compound (C) may be reacted with diethyl sulfate in the presence of a base and a phase transfer catalyst. The base comprises one or more of sodium hydroxide, potassium hydroxide, lithium hydroxide, calcium hydroxide, sodium carbonate, potassium carbonate, sodium bicarbonate, potassium bicarbonate, sodium hydroxide, and potassium hydride. In particular, potassium hydroxide may be used. The phase transfer catalyst comprises one or more of tetrabutyl ammonium bromide (TBAB), tetrabutyl ammonium iodide (TBAI), benzyl triethyl ammonium chloride (TEBAC), polyethylene Glycol (PEG-200, 400, 600, 800, 1000), crown ethers selected from 12-crown-4, 15-crown-5, 18-crown-6, dibenzo-18-crown-6, and diaza-18-crown-6. In particular, the phase transfer catalyst may be TBAB.

The process embodiment involves partitioning the reaction mixture after completion of the reaction by water. The toluene layer may be distilled under vacuum and degassed. The residue may be further distilled to remove excess diethyl sulfate and treated with alcohols selected from methanol, ethanol, isopropanol, and butanol. In particular, ethanol may be used.

The ethanolic solution of residue may be charcoalized and filtered. The filtrate may be treated with triethylamine at reflux temperature from about 75° C. to 85° C. followed by removal of ethanol and treating with ethyl acetate. The compound (B) may be obtained in form of oil and may be preceded further.

In general; the compound (B) may be deprotected i.e. debenzylation in the presence of catalyst. The catalyst for debenzylation comprises one or more of Pd/C, Raney Nickel, Vitride, and LiAlH$_4$. In particular, Pd/C may be used for debenzylation under autoclave conditions.

The hydroxy compound (A) may be obtained by usual work-up procedure involving use organic solvents. In particular, the organic solvent comprises one or more of alcohols selected from methanol, ethanol, isopropanol, 2-propanol, 1-butanol, and t-butyl alcohol; ketones selected from acetone, butanone, and methyl isobutyl ketone; esters selected from ethyl acetate, isopropyl acetate, t-butyl acetate, and isobutyl acetate, chlorinated hydrocarbons selected from methylene dichloride, ethylene dichloride, and chlorobenzene, aromatic.hydrocarbons selected from toluene, xylene, and ethylbenzene; aliphatic hydrocarbons selected from pentane, hexane, heptane, and cyclohexane; ethers selected from tetrahydrofuran, 1,4-dioxane, diisopropyl ether, diethylether, and methyl tert-tertbutyl ether. In particular, the mixture of diisopropyl ether and n-heptane may be used.

The hydroxy compound (A) obtained is crystalline characterized by X-ray powder diffraction. The crystalline hydroxy compound (A) is having an X-ray powder diffraction having characteristic peaks expressed in degrees 2θ (±0.2° 2θ) at about 7.0, 13.4, 13.9, 14.6, 15.3, 16.6, 19.0, 21.7, 22.1, 23.5, 24.4, 26.1, 26.8 and 29.5±0.2° 2θ.

In another general aspect, there is provided a process for the preparation of mesylate compound of Formula (A1),

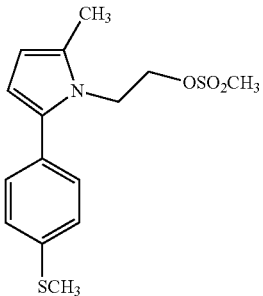

the process comprising:
(a) reacting 2-bromo-1-(4-(methylthio)phenyl)ethanone (E1) with methyl acetoacetate in one or more organic solvents in the presence of a base to obtain compound (D1);

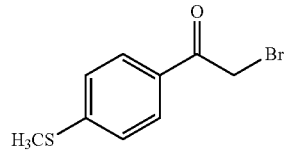

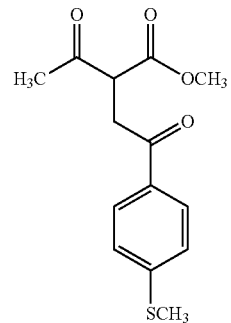

(b) hydrolyzing the compound (D1) with a base followed by decarboxylation to obtain compound (C1);

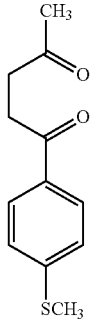

(c) reacting the compound (C1) with ethanolamine under Paal-Knorr conditions in the presence of an acid to obtain compound (B1); and

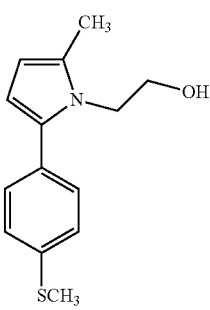

(B1)

(d) reacting the compound (B1) with methane sulphonyl chloride in the presence of a base in one or more organic solvents to obtain the mesylate compound (A1).

In general, the organic solvent comprises one or more of esters selected from ethyl acetate, isopropyl acetate, t-butyl acetate, and isobutyl acetate; hydrocarbons selected from toluene, xylene, ethyl benzene, heptane, hexane, and cyclohexane; chlorinated solvents selected from methylene dichloride, ethylene dichloride, chlorobenzene, chloroform, and carbontetrachloride.

The base in step (a) comprises one or more of sodium hydroxide, potassium hydroxide, lithium hydroxide, calcium hydroxide, sodium carbonate, potassium carbonate, sodium bicarbonate, potassium bicarbonate, sodium hydroxide, potassium hydride, sodium methoxide, potassium tert-butoxide, and sodium pentoxide. In particular, sodium methoxide may be used.

The embodiments of the process may further include in-situ hydrolyzing the compound (D1) without isolating from step (a) as the scope of the invention.

The compound (D1) may be hydrolyzed with same or different base as disclosed herein above. In particular, the base for hydrolysis comprises one or more of sodium hydroxide, potassium hydroxide, lithium hydroxide, calcium hydroxide, sodium carbonate, potassium carbonate, sodium bicarbonate, potassium bicarbonate, sodium hydroxide, potassium hydride, sodium methoxide, potassium tert-butoxide, and sodium pentoxide. More particularly, sodium hydroxide may be used.

The reaction mixture may be preferably diluted with one or more of other organic solvents. The other organic solvent comprises one or more of alcohols selected from methanol, ethanol, isopropanol, 2-propanol, 1-butanol, and t-butyl alcohol; ketones selected from acetone, butanone, and methylisobutyl ketone; esters selected from ethyl acetate, isopropyl acetate, t-butyl acetate, and isobutyl acetate. In particular, methanol may be used.

The compound (C1) may be obtained by decarboxylation of carboxylic acid derivative obtained in-situ which may not be isolated.

In general, the compound (B1) may be obtained by treating the diketo compound (C1) with ethanolamine under Paal-Knorr conditions in the presence of an acid. The acid comprises one or more of acetic acid, hydrochloric acid, sulfuric acid, formic acid, hydrobromic acid, trifluoroacetic acid, and pivalic acid. In particular, pivalic acid may be used.

Optionally, the compound (B1) may be proceeded for further reaction in-situ. The compound (B1) obtained in step (c) may be reacted with methane sulphonyl chloride in toluene in the presence of a base.

The base for step (d) comprises one or more of inorganic bases selected from sodium hydroxide, potassium hydroxide, lithium hydroxide; sodium carbonate, potassium carbonate, sodium bicarbonate, potassium bicarbonate; and ammonia or its aqueous solution; and organic bases selected from methyl amine, ethyl amine, TEA, TBA, DIPA, DIPEA, pyridine, piperidine, morpholine, DBU, DABCO or DBN. In particular, TEA may be used.

The compound (A1) may be isolated by removal of toluene by distillation followed by treating the residue with methanol and removal of methanol to obtain wet-cake. The wet product may be dried in vacuum tray dryer to obtain crystalline mesylate compound of Formula (A1).

The crystalline mesylate compound (A1) is having an X-ray powder diffraction having characteristic peaks expressed in degrss $2\theta$ ($\pm 0.2°$ $2\theta$) at about 12.4, 15.0, 17.7 and $23.2\pm 0.2°$ $2\theta$.

Powder X-ray Diffraction of saroglitazar magnesium can be obtained under following conditions.

Powder X-Ray Diffraction: X-ray powder diffraction spectrum was observed on a MF 2100 2 KW X-ray Powder diffractometer of make Rigaku having a Copper K$\alpha$-radiation at a voltage of 40 kV and 30 mA. Approximately 150 mg sample was gently flattened on a quartz plate without further processing (e.g. Grinding and sieving) and scanned from 4° to 40° at 0.010° sampling width and 4.000° per minute. Any other X-ray powder diffractometer of similar conditions may also be used.

In another general aspect, saroglitazar magnesium alongwith its intermediates may be prepared by the reaction scheme-1, scheme-2 and scheme-3 as shown below, which is also the scope of the present invention.

Scheme-1

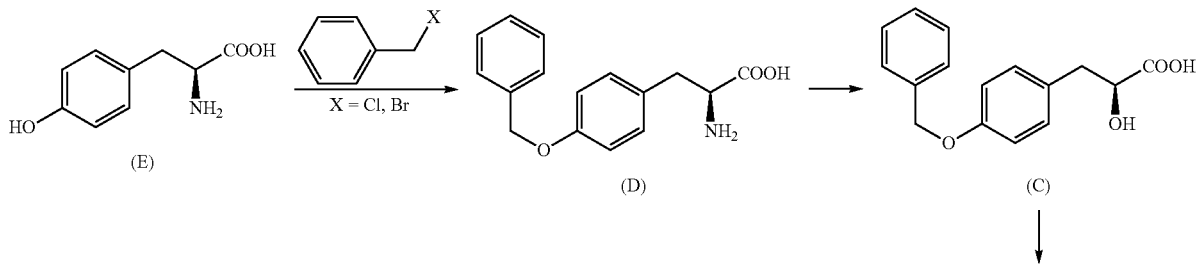

-continued
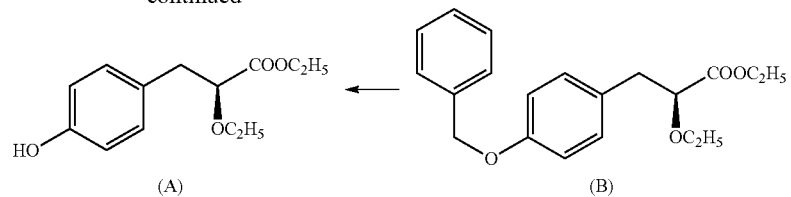
Scheme-2
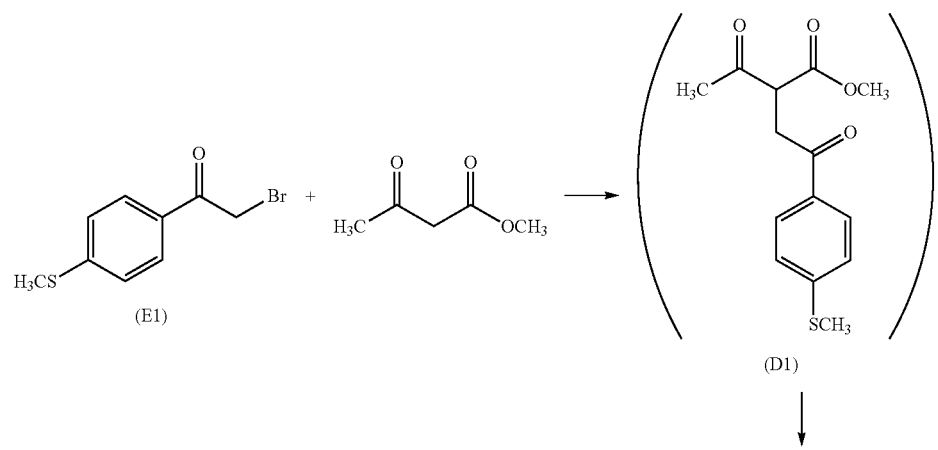
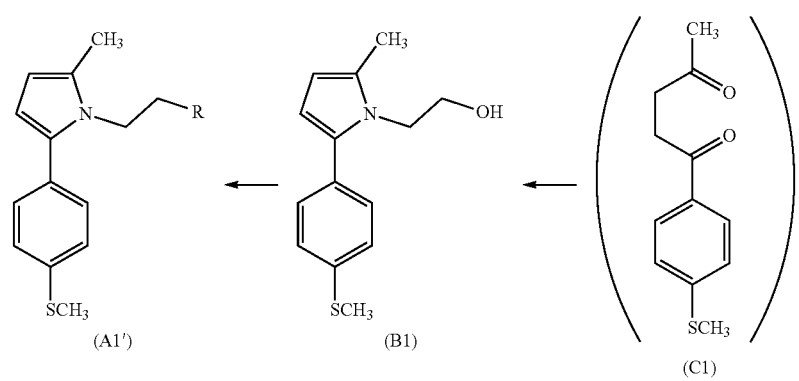
whererin R represents suitable hydroxy leaving group like mesylate, tosylate and triflate group.

Scheme-3

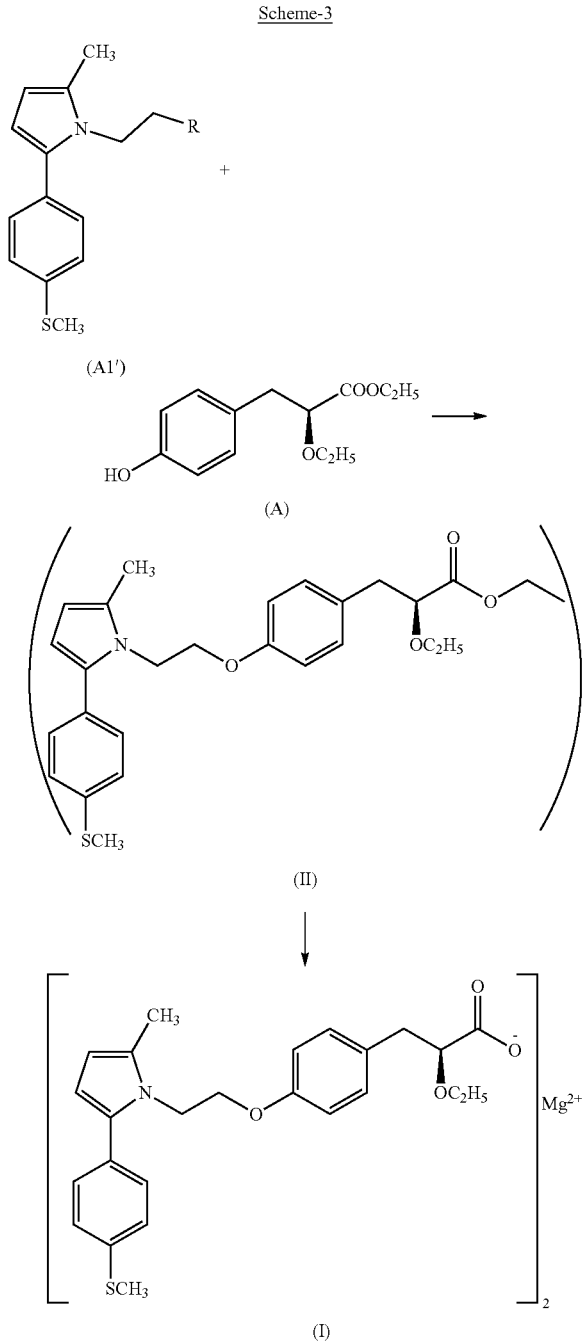

wherein R represents suitable hydroxy leaving group like mesylate, tosylate and triflate group.

The invention also encompasses pharmaceutical compositions comprising saroglitazar of the invention. As used herein, the term "pharmaceutical compositions" includes pharmaceutical formulations comprises one or more of tablets, pills, powders, liquids, suspensions, emulsions, granules, capsules, suppositories, and injection preparations.

Pharmaceutical compositions containing the saroglitazar of the invention may be prepared by using diluents or excipients selected from fillers, bulking agents, binders, wetting agents, disintegrating agents, surface active agents, and lubricants.

Various modes of administration of the pharmaceutical compositions of the invention can be selected depending on the therapeutic purpose, for example tablets, pills, powders, liquids, suspensions, emulsions, granules, capsules, suppositories, or injection preparations.

In another general aspect, there is provided a pharmaceutical composition comprising substantially amorphous form of saroglitazar magnesium having a particle size distribution having D(10) of about 10 μm or less, D(50) of about 25 μm or less and D(90) of about 100 μm or less together with one or more pharmaceutically acceptable carriers, excipients or diluents.

In another general aspect, there is provided a pharmaceutical composition comprising substantially amorphous form of saroglitazar magnesium together with one or more pharmaceutically acceptable carriers, excipients or diluents.

The present invention is further illustrated by the following example which is provided merely to be exemplary of the invention and do not limit the scope of the invention. Certain modification and equivalents will be apparent to those skilled in the art and are intended to be included within the scope of the present invention.

EXAMPLES

Example—1

Preparation of (S)-2-amino-3-(4-(benzyloxy)phenyl) propanoic acid (D)

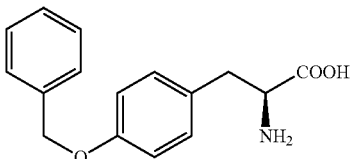

In a 5 Liter three necked round bottom flask equipped with nitrogen atmosphere facility, mechanical stirrer, thermometer and an addition funnel, L-tyrosine (100 g), sodium hydroxide (24.28 g) solution in water (276 ml) and cupric sulfate pentahydrate (82.6 g) solution in water (276 ml) were added at room temperature. The reaction mixture was heated to reflux temperature for 1 hour and cooled to 20° to 30° C. Methanol (1990 mL) was added and subsequently sodium hydroxide (24.28 g) solution in water (276 ml) and benzyl bromide solution (113.2 g) were added. The reaction mixture was heated to 60° C.-65° C. and maintained for 4 hours and cooled to 20° to 30° C. The reaction mixture was filtered and washed with water-methanol mixture (1:2) and dried for 30 min. The wet-cake was treated with HCl solution (162.0 ml) in water (944 ml) and resulting reaction mixture was cooled to 15° to 20° C. and stirred for 30 min. The reaction mixture was filtered and washed with water. The wet-cake was treated with aqueous liquor ammonia solution (1105 ml) and stirred for 1 hour. The product was filtered and washed with water and dried to obtain 110 g of compound (D).

Example—2

Preparation of (S)-3-(4-(benzyloxy)phenyl)-2-hydroxypropanoic acid (C)

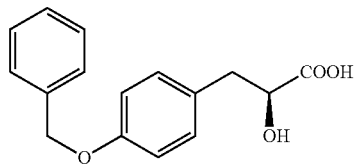 [SMILES: O=C(O)[C@@H](O)Cc1ccc(OCc2ccccc2)cc1]

In a 5 Liter three necked round bottom flask equipped with nitrogen atmosphere facility, mechanical stirrer, thermometer and an addition funnel, DMSO (650 ml) was charged with 100 g of compound (D) as obtained in example 1. The reaction mixture was added with $H_2SO_4$ solution (48.0 g) in 400 ml water and stirred to get the clear solution. The reaction mixture was cooled to −5° to 0° C. and sodium nitrite solution were added subsequently and stirred for 2 hours. The reaction mixture was raised to 15° C. to 25° C. and stirred for 1 hour. Water 1000 ml and 1000 ml of ethyl acetate were added and reaction mixture was stirred for 1 hour and filtered and treated with 400 ml of ethyl acetate and allowed to settle. The separated aqueous layer was treated with 200 ml of ethyl acetate 500 ml of water. The organic layer was treated with 10% sodium chloride solution and allowed to settle. The organic layer was separated and charcoalized and dried over sodium sulfate. The reaction mixture was filtered and washed with 100 ml of ethyl acetate. The filtrate was distilled and residue was treated with 5 ml of DMSO. The reaction mixture was heated to 60° to 65° C. and cooled to 5° to 10° C. and filtered. The product was washed with ethyl acetate and dried in hot air oven for 12 hours at 50° to 55° C.

Example—3

Preparation of (S)-ethyl 3-(4-(benzyloxy)phenyl)-2-ethoxypropanoate (B)

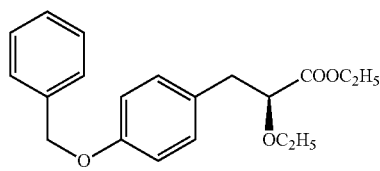

In a 5 Liter three necked round bottom flask equipped with nitrogen atmosphere facility, mechanical stirrer, thermometer and an addition funnel, 1900 ml of toluene was charged, 200 g of compound (c), 100 ml of toluene, 1133.6 g (963.1 ml) of diethyl sulphate and TBAB (40 g) was added and stirred for 5-10 min at room temperature. The reaction mixture was cooled to 10-15° C. and 20.6 g of potassium hydroxide powder were gradually added and the reaction mixture was stirred for 2 hours. The mixture was filtered through hyflow bed and slurry washed with toluene. In another three necked round bottom flask 2000 ml of water was cooled to 5° to 10° C. and above filtrate was added and stirred for 15 min. the separated aqueous layer was extracted with 200 ml of toluene. The separated toluene layer was washed with 1000 ml water and 400 ml of 20% sodium chloride solution at 25° to 35° C. The reaction mixture was filtered through hyflow bed and washed with 200 ml of toluene. The reaction mixture was distilled under vacuum at 45° C. to 50° C. and degassed for 2 hours. The diethyl sulfate was distilled out under high vacuum at 65° to 76° C. and the residue was diluted with 837 ml of ethanol and charcoalized and filtered. The bed was washed with ethanol 279 ml, and filtrated. The filtrated was added triethylamine (69.55 g) and heated to reflux for 6 hr and cooled to 60° to 65° C. The reaction mixture was again charcoalized cooled atmospherically to 25° to 30° C., filtered and washed with ethanol. The ethanol was distilled out under vacuum completely and the residue was cooled to 25° to 30° C. Ethyl acetate (1000 ml) and water (1000 ml) were added and reaction mixture was stirred for 30 min. The separated ethyl acetate layer was washed with $NaHCO_3$ solution (400 ml) and water 1000 ml. The ethyl acetate layer was washed with sodium chloride solution to and dried over anhydrous sodium sulphate and charcoalized. The reaction mixture was filtered and washed with ethyl acetate. The filtrate was collected and oil residue was obtained.

Example 4

Preparation of 2-Ethoxy-3-(4-hydroxy-phenyl)-propionic acid ethyl ester (A)

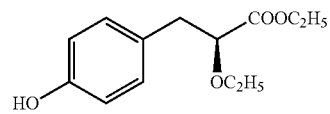

In a 2 Liter three necked round bottom flask equipped with nitrogen atmosphere facility, mechanical stirrer, thermometer and an addition funnel, compound (B) (100 g) as obtained in example 3, ethanol (600 ml) and activated carbon 10 g were stirred for 30 min at 20° C. to 30° C. and filtered. The filtrate was added with palladium charcoal (10%) 0.25 g and stirred for 30 min. The filtered reaction mixture washed with 75 ml ethanol. The filtrate as obtained was treated with triethylamine (4.0 ml) and palladium catalyst (1.0 g). $N_2$ and $H_2$ were flushed and maintained the pressure up to 5.0 kg for 4 hours in an autoclave reactor. Palladium charcoal (2.0 g) was added and maintained the temperature and pressure till hydrogen consumption stops. The reaction mixture was filtered and washed with ethanol (100 ml). The filtrate was distilled out and degassed for 60 min at 45° C. to 50° C., diisopropyl ether (31.5 ml) and n-heptane (126 ml) were added and the reaction mixture was cooled to 25° C. to 30° C. and dried for 15-20 min.

The product was further dried under vacuum for 8 hours. The compound (A) was characterized as crystalline solid by x-ray powder diffraction (FIG. 2).

Example 5

Preparation of Methanesulfonic Acid 2-[2-methyl-5-(4-methylsulfanyl-phenyl)-pyrrol-1-yl]-ethyl ester (A1)

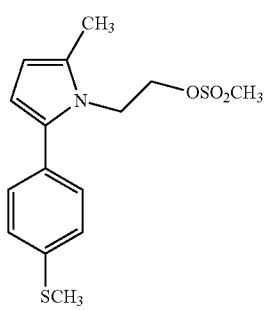

In a 5 Liter three necked round bottom flask equipped with nitrogen atmosphere facility, mechanical stirrer, thermometer and an addition funnel, sodium methoxide (165 g) and toluene (1000.0 ml) were added under nitrogen environment and cooled to 8° C. to 12° C. Methyl acetoacetate (331.55 g) was added dropwise and stirred for 1 hour. 2-bromo-1-(4-methyl sulfonyl phenyl) ethanone (500.0 g) compound (E1) in toluene (1500.0 ml) and sodium sulfate (75.0 g) mixture was stirred for 10 min and filtered at 25° to 35° C. The filtrate as obtained was added dropwise into the previous reaction mixture and stirred at 30° C. to 35° C. for 30 min. The organic layer was collected and washed with 10% sodium bicarbonate solution. The separated organic layer was collected and washed with water. 2-[2-(4-Methyl sulfanyl-phenyl)-2-oxo-ethyl]-3-oxo-butynic acid methyl ester as obtained in toluene layer is diluted with methanol (2500 ml) and sodium hydroxide solution (89.75 g) in water (2500 ml) was added and heated to 50° to 55° C. for 1 hour. The layers were separated and the toluene layer was collected and heated to 45° to 55° C. and charcoalized. The reaction mixture was filtered and pivalic acid (57.3 g) and ethanol amine (143.9 g) were added and heated to 105° to 115° C. for removing water azeotropically. The toluene layer was separated and triethyl amine (271.85 g) was added at 25° to 35° C. and the reaction mixture was cooled to 10° to 20° C. Methane sulphonyl chloride (282.5 g) was added dropwise, and stirred for 2 hours and heated to 35° to 45° C. The reaction mixture was filtered and washed with toluene. Toluene was distilled out completely under the vacuum, methanol (2500 ml) was added and heated to 55° to 65° C. and charcoalized for 30 min. The reaction mixture was filtered and washed with methanol. The reaction mixture was cooled to 25° to 35° C. and stirred for 30 min. Reaction mass was further cooled to −5° to 5° C. and filtered. The wet-cake was washed with methanol and dried to obtain compound (A1). The compound (A) was characterized as crystalline solid by x-ray powder diffraction (FIG. 3).

Example—6

Preparation of Saroglitazar Magnesium (I)

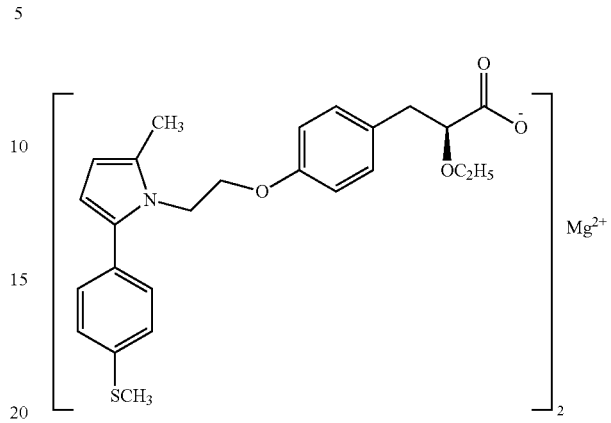

In a 5 Liter three necked round bottom flask equipped with nitrogen atmosphere facility, mechanical stirrer, thermometer and an addition funnel, 2-ethoxy-3-(4-hydroxy-phenyl)-propionic acid ethyl ester (A) (100.0 g) and cyclohexane (1300.0 ml) were charged and reaction mixture was heated to 45° to 55° C. Potassium carbonate (58.0 g) was added and stirred for 30 min. methanesulfonic acid 2-[2-methyl-5-(4-methylsulfanyl-phenyl)-pyrrol-1-yl]-ethyl ester (A1) (150.24 g), 18-Crown-6 (5.0 g) and THF (200.0 ml) were added and heated to 75° C. to 85° C. for 36 hours. The reaction mixture was cooled to 25° to 35° C. and water (1000.0 ml) was added and stirred for 15 min. The separated aqueous layer was treated with cyclohexane (200.0 ml) and stirred for 15 min. The organic layers were combined and washed with caustic solution (600.0 ml). The separated organic layer was washed with water (600.0 ml) and charcoalized with (5.0 g) charcoal and stirred for 30 min and filtered. The filtrate was distilled to remove cyclohexane and the residue was collected. The residue as obtained was treated with ethanol (400.0 ml) and stirred for 15 min. Sodium hydroxide 20.14 g solution in water (200.0 ml) was added and the reaction mixture was stirred for 3 hours. The reaction mixture was diluted with water (1800.0 ml) and stirred for 15 min. The separated aqueous layer was washed with n-butyl acetate. The separated aqueous layer was added magnesium acetate tetrahydrate solution (90.0 g) in water (100.0 ml) and stirred for 1 hour. The aqueous layer was extracted with methylene dichloride (200 ml). The separated organic layer was washed with sodium chloride solution and charcoalized. The charcoalized solution was filtered and filtrate was distilled to remove methylene dichloride completely. The residue was diluted with methylene dichloride (1000 ml) and stirred for 30 min. The organic solution was added into n-heptane (1500 mL) and stirred for 3 hours. The product was filtered and washed with n-heptane and dried in vacuum tray dryer at 25° C. to 30° C. for 3 hours. The product was sieved through 0.5 mm sieve and milled through jet-milled. The product was further dried in vacuum tray drier at 40° C. to 50° C. for 6 hours followed by drying at 55° C. to 65° C. for 40 hours to obtain substantially amorphous form of saroglitazar magnesium (I). The compound is characterized by X-ray power diffraction (FIG. 1). Purity>98% by area percentage of HPLC. Chiral Purity>99% by area percentage of HPLC.

PSD: D(0.1): 5.87 µm, D(0.5): 16.92 µm, D(0.90): 53.30 µm.

Residual solvents: Cyclohexane<0.3%, Tetrahydrofuran<0.07%, ethanol<0.3%, n-butyl acetate<0.5%, methylene dichloride<0.06% and n-heptane<0.5% by GC.

Example—7

Preparation of Pharmaceutical Dosage Form of Saroglitazar Magnesium (I)

Procedure for preparation of saroglitazar dosage form comprises;

The active ingredient (Saroglitazar magnesium) with pharmaceutically acceptable carriers, excipients or diluents selected from microcrystalline cellulose, lactose, magnesium oxide, povidone, talc, magnesium stearate, croscarmellose sodium and colloidal silicon dioxide.

While the present invention has been described in terms of its specific embodiments, certain modifications and equivalents will be apparent to those skilled in the art and are intended to be included within the scope of the present invention.

We claim:

1. A process for the preparation of saroglitazar magnesium of Formula (I),

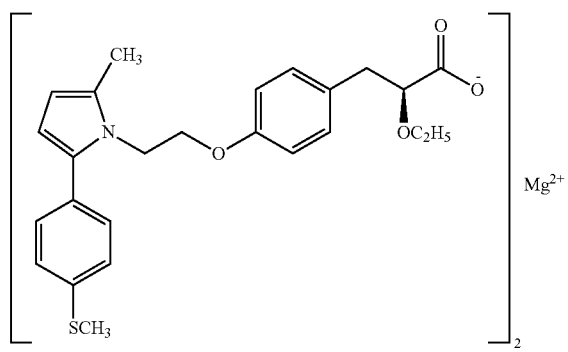

(I)

the process comprising:
(a) reacting a hydroxy compound (A) with a mesylate compound (A1) in a mixture of organic solvents comprising cyclohexane in the presence of a base and a phase transfer catalyst at a temperature between 35° C. and 85° C. to obtain an alkoxy ester compound of Formula (II);

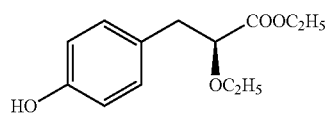

(A)

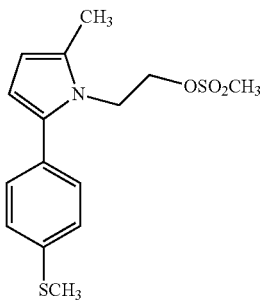

(A1)

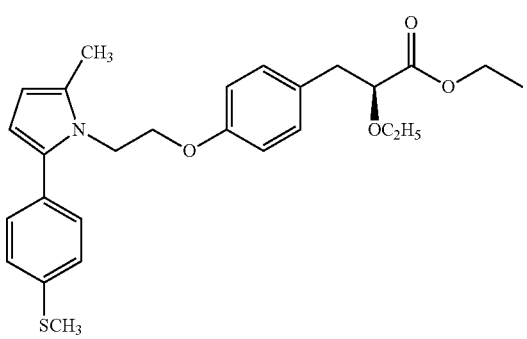

(II)

(b) hydrolyzing the alkoxy ester compound of Formula (II) with a base to obtain saroglitazar; and
(c) reacting the saroglitazar with a magnesium source to obtain saroglitazar magnesium of Formula (I).

2. The process according to claim 1, wherein the mixture of organic solvents further comprises one or more of alcohols selected from methanol, ethanol, isopropanol, 2-propanol, 1-butanol, and t-butyl alcohol; ketones selected from acetone, butarione, and methyl isobutyl ketone; esters selected from ethyl acetate, isopropyl acetate, t-butyl acetate, and isobutyl acetate; chlorinated hydrocarbons selected from methylene dichloride, ethylene dichloride, and chlorobenzene; hydrocarbons selected from pentane, hexane, and heptane; or ethers selected from tetrahydrofuran, 1,4-dioxane, diisopropyl ether, diethyl ether, and methyl tert-butyl ether.

3. The process according to claim 1, wherein in step (a), the base comprises one or more of sodium hydroxide, potassium hydroxide, lithium hydroxide, calcium hydroxide, sodium carbonate, potassium carbonate, sodium bicarbonate, potassium bicarbonate, sodium hydride, potassium hydride, potassium tert-butoxide, and sodium pentoxide.

4. The process according to claim 1, wherein the phase transfer catalyst comprises one or more of tetrabutyl ammonium bromide (TBAB), tetrabutyl ammonium iodide (TBAI), benzyl triethyl ammonium chloride (TEBAC), a polyethylene Glycol, or a crown ether selected from the group consisting of 12-crown-4, 15-crown-5, 18-crown-6, dibenzo-18-crown-6, and diaza-18-crown-6.

5. The process according to claim 1, wherein in step (b), the base comprises one or more of sodium hydroxide, potassium hydroxide, lithium hydroxide, calcium hydroxide, sodium carbonate, potassium carbonate, sodium bicarbonate, potassium bicarbonate, sodium hydride, and potassium hydride.

6. A process for the preparation of saroglitazar of Formula (IA), or a pharmaceutically acceptable salt thereof,

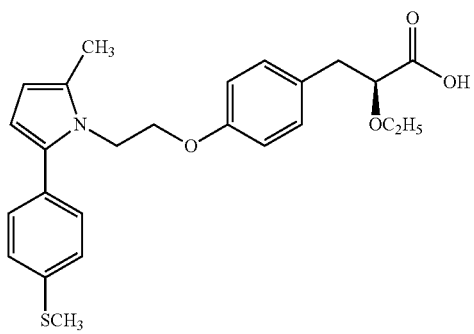
(IA)

the process comprising:
(a) reacting a hydroxy compound (A) with a compound of Formula (A1') in a mixture of organic solvents comprising cyclohexane in the presence of a base and a phase transfer catalyst at a temperature between 35° C. to 85° C. to obtain an alkoxy ester compound of Formula (II),

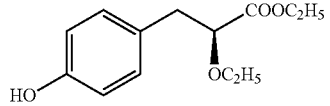
(A)

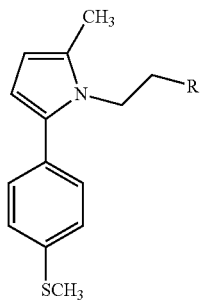
(A')

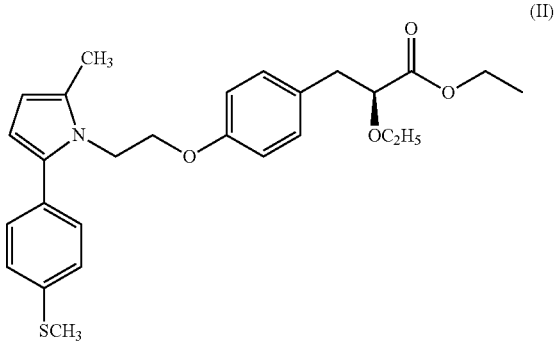
(II)

wherein, R is mesylate, tosylate, or triflate;
(b) hydrolyzing the alkoxy ester compound of Formula (II) with a base to obtain saroglitazar of formula (IA); and
(c) optionally, converting the saroglitazar to a pharmaceutically acceptable salt thereof.

* * * * *